United States Patent
Lynch et al.

(10) Patent No.: US 10,660,923 B2
(45) Date of Patent: May 26, 2020

(54) SINUSITIS DIAGNOSTICS AND TREATMENTS

(71) Applicant: The Regents of the University of California, Oakland, CA (US)

(72) Inventors: Susan Lynch, Piedmont, CA (US); Andrew Goldberg, Mill Valley, CA (US); Steve D. Pletcher, Mill Valley, CA (US)

(73) Assignee: The Regents of the University of California, Oakland, CA (US)

( * ) Notice: Subject to any disclaimer, the term of this patent is extended or adjusted under 35 U.S.C. 154(b) by 62 days.

(21) Appl. No.: 15/203,428

(22) Filed: Jul. 6, 2016

(65) Prior Publication Data
US 2016/0310546 A1    Oct. 27, 2016

Related U.S. Application Data

(63) Continuation of application No. 14/394,006, filed as application No. PCT/US2013/036297 on Apr. 12, 2013, now abandoned.

(60) Provisional application No. 61/624,105, filed on Apr. 13, 2012.

(51) Int. Cl.
| | |
|---|---|
| *A61K 35/747* | (2015.01) |
| *A61K 35/744* | (2015.01) |
| *C12Q 1/06* | (2006.01) |
| *C12Q 1/689* | (2018.01) |
| *A61K 9/00* | (2006.01) |

(52) U.S. Cl.
CPC .......... *A61K 35/747* (2013.01); *A61K 9/0043* (2013.01); *A61K 35/744* (2013.01); *C12Q 1/06* (2013.01); *C12Q 1/689* (2013.01)

(58) Field of Classification Search
None
See application file for complete search history.

(56) References Cited

U.S. PATENT DOCUMENTS

| | | | |
|---|---|---|---|
| 6,767,537 B2 | 7/2004 | Nicolay | |
| 7,173,007 B1 * | 2/2007 | Zaiou | A61K 38/1709 435/440 |
| 2005/0202476 A1 * | 9/2005 | Saettler | C12Q 1/689 435/134 |
| 2007/0196434 A1 * | 8/2007 | Alimi | A61K 33/00 424/434 |
| 2008/0102061 A1 * | 5/2008 | Sobol | A23C 9/133 424/93.44 |
| 2008/0254058 A1 | 10/2008 | Glenting et al. | |
| 2009/0214497 A1 | 8/2009 | Park et al. | |
| 2009/0274672 A1 | 11/2009 | Yu et al. | |
| 2010/0189702 A1 | 7/2010 | Drake et al. | |
| 2015/0079039 A1 | 3/2015 | Lynch et al. | |

FOREIGN PATENT DOCUMENTS

| | | |
|---|---|---|
| EP | 2361632 A1 | 8/2011 |
| WO | WO-00/78322 A2 | 12/2000 |
| WO | WO-00/78322 A3 | 12/2000 |
| WO | WO-2012/019058 A1 | 2/2012 |
| WO | WO-2012/019058 A9 | 2/2012 |

OTHER PUBLICATIONS

Park et al., "New functional probiotic Lactobacillus sakei probio 65 alleviates atopic symptoms in the mouse", Journal of Medicinal Food, 2008, 11(3), pp. 405-12.*
Ghaffar et al., "Expression of IgE heavy Chain Transcripts in the Sinus Mucosa of Atopic and Nonatopic Patients with Chronic Sinusitis", American Journal of Respiratory Cell and Molecular Biology, 1998, vol. 18, pp. 706-711.*
Stressmann et al., "Characterization of bacterial community diversity in chronic rhinosinusitis infections using novel culture-independent techniques", American Journal of Rhinology and Allergy, 2011, vol. 25, pp. e133-e140.*
Wellinghausen et al., "A fatal case of necrotizing sinusitis due to toxigenic Corynebacterium ulcerans", International Journal of Medical Microbiology, 2002, vol. 292, pp. 59-63.*
International Search Report and Written Opinion dated Jul. 29, 2013, for PCT Application No. PCT/US2013/036297.
Bernard, K.A. et al. (Jan. 1991). "Cellular fatty acid composition as an adjunct to the identification of asporogenous, aerobic gram-positive rods," *J Clin Microbiol* 29(1):83-89.
Fokkens, W.J. et al. (Mar. 2012). "EPOS 2012: European position paper on rhinosinusitis and nasal polyps 2012. A summary for otorhinolaryngologists," *Rhinology* 50(Supplement 23):1-329.
Jousimies-Somer, H.R. et al. (Dec. 1989). Comparison of the nasal bacterial floras in two groups of healthy subjects and in patients with acute maxillary sinusitis, *J Clin Microbiol* 27(12):2736-2743.

* cited by examiner

*Primary Examiner* — Laura Schuberg
(74) *Attorney, Agent, or Firm* — Edward D. Grieff; Mintz, Levin, Cohn, Ferris, Glovsky and Popeo, P.C.

(57) ABSTRACT

Provided herein are compositions for improving sinus microbiota and treating sinusitis. Further provided are methods of detecting imbalance in the sinus microbiota that can be indicative of sinusitis, and methods of determining whether an individual has or is at risk of developing sinusitis, e.g., chronic sinusitis.

20 Claims, 8 Drawing Sheets
Specification includes a Sequence Listing.

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
actcctacgg gaggcagcag                                               20

<210> SEQ ID NO 2
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 2
attaccgcgg ctgctgg                                                  17

<210> SEQ ID NO 3
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 3
gaacggaaag gccctgcttg ca                                            22

<210> SEQ ID NO 4
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 4
ggctcctatc cggtattaga cc                                            22

<210> SEQ ID NO 5
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 5
```

```
ggtaaaggct caccaagacc gtgat                                              25

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
tcacgcggcg ttgctccatc                                                    20

<210> SEQ ID NO 7
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 7
tgtggcggga aagacagc                                                      18

<210> SEQ ID NO 8
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 8
ccttcctatg gcttagcttc agc                                                23

<210> SEQ ID NO 9
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 9
caccacacct tctacaatga gctgc                                              25

<210> SEQ ID NO 10
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 10
acaccctgga tagcaacgta catgc                                              25
```

SINUSITIS DIAGNOSTICS AND TREATMENTS

CROSS-REFERENCE TO RELATED APPLICATIONS

This application is a continuation of U.S. application Ser. No. 14/394,006 filed Oct. 10, 2014, abandoned, which is a § 371 US National Stage of PCT/US2013/036297 filed Apr. 12, 2013, which claims priority to U.S. Application No. 61/624,105 filed Apr. 13, 2012, the disclosures of which are incorporated by reference in their entirety.

REFERENCE TO SUBMISSION OF A SEQUENCE LISTING AS AN ASCII TEXT FILE

The Sequence Listing written in file 48536-518C01US_ST25.TXT, created on Jul. 1, 2016, 2,382 bytes, machine format IBM-PC, MS-Windows operating system, is hereby incorporated by reference.

BACKGROUND OF THE INVENTION

Sinusitis (rhinosinusitis) is one of the most common problems presented to the primary care practitioner in the ambulatory setting, affecting more than 15% of the US population annually, resulting in over $5.8 billion in direct health care expenditures (1). Typically classified by duration of symptoms, sinusitis may be acute (less than 4 weeks in duration), sub-acute (4-12 weeks) or chronic (more than 12 weeks, with or without acute exacerbations).

Chronic Rhinosinusitis (CRS), represents a large portion of sinusitis cases, affecting more than 30 million Americans (2), resulting in an annual economic health care burden in excess of $2.4 billion. Culture-based studies have demonstrated chronic bacterial and/or fungal colonization of CRS patient sinus cavities implicating these species in the pathophysiology of CRS. Despite these findings, the microbiology and immunology underlying CRS remains poorly described, controversial, and to date no clear etiology has been described (3). Known bacterial pathogens, such as *Staphylococcus* and *Streptococcus* species isolated from CRS sinuses and implicated in the disease (4-7), have also been detected in the nasopharynx of healthy individuals with no sinus symptomology (8). These results indicate that the composition of the microbiota at discrete mucosal sites may define the abundance and pathogenic behavior of specific members of the assemblage. Such observations suggest that local microbiota composition plays a key role in protection against pathogen overgrowth and virulence gene expression, and that perturbations to local microbiota composition can contribute to infectious and inflammatory disease etiology.

The sinuses are lined with respiratory epithelia that support colonization by a diverse microbiome at upper respiratory sites, e.g., oropharynx (8, 11). Little is known of the composition of the resident microbiome of the paranasal sinuses and the contribution of these assemblages to sinus mucosal health. Microbiological studies of this niche are based on culture-based approaches, which under-estimate the diversity of species present. The present disclosure describes results from culture-independent approaches, and thus provides a more accurate picture of sinus microbiome composition. The presently disclosed results show comparative analyses of healthy and diseased (sinusitis) samples, revealing both gross community characteristics and discrete species highly associated with health status.

BRIEF SUMMARY OF THE INVENTION

Described herein are results from a high-resolution, culture-independent comparative analysis of the sinus microbiota of chronic rhinosinusitis (CRS) patients, and healthy subjects without CRS undergoing open nasal or sinus surgery. Surgical patients typically exhibit severe disease, and surgery provides access to affected sinus mucosal surfaces that are otherwise inaccessible. The results indicate that specific features of the sinus mucosal microbiota are associated with disease state and severity, and identify both pathogenic and protective species in this niche.

Provided herein are novel probiotics for improving the sinus microbiota in an individual comprising at least one bacteria listed in Table X, e.g., a Lactic Acid Bacterial (LAB) species, a *Lactobacillus* species, or *L. sakei*. Such probiotics can be used to treat an individual with reduced microbial diversity in the nasal sinus, or one that has been diagnosed with acute or chronic sinusitis. In some embodiments, provided is a pharmaceutical composition comprising at least one bacterial species listed in Table X, and a pharmaceutically acceptable excipient, e.g., for nasal or sinus administration. In some embodiments, the composition comprises at least 2, 3, 4, 5, 6, 7, 8, 9, 10, 20, 30, 40, 50, 100, or more of the bacteria listed in Table X. In some embodiments, the composition comprises at least one LAB species. In some embodiments, the composition comprises *L. sakei*. In some embodiments, the composition consists essentially of *L. sakei*, that is, other bacterial species, if present at all, are not detectable, or not present in quantities sufficient to colonize the sinonasal mucosa.

Further provided are methods for improving the sinus microbiota (e.g., increasing the microbial diversity, increasing the relative amount of beneficial bacteria such as those listed in Table X, or reducing the level of pathogenic bacteria such as Corynebacteria) in an individual comprising administering at least one bacteria listed in Table X (e.g., a Lactic Acid Bacterial (LAB) species, a *Lactobacillus* species, or *L. sakei*); and allowing the bacteria to colonize the sinonasal mucosa. Such methods can be used to treat an individual diagnosed with sinusitis, or displaying sinusitis symptoms. In some embodiments, the administering is nasal, e.g., using a spray, aerosol, syringe, irrigation, or nasal drops. In some embodiments, the maxillary sinus is colonized. In some embodiments, the ethmoid sinus is colonized. In some embodiments, the frontal sinus is colonized. In some embodiments, the sphenoid sinus is colonized.

In some embodiments, at least 2, 3, 4, 5, 6, 7, 8, 9, 10, 20, 30, 40, 50, 100, or more of the bacteria listed in Table X are administered. In some embodiments, at least one Lactic Acid Bacterial (LAB) species is administered. In some embodiments, *Lactobacillus sakei* is administered. In some embodiments, *L. sakei* is the only bacteria administered in an effective amount (e.g., sufficient to colonize the sinonasal mucosa).

In some embodiments, the method further comprises detecting the microbial diversity of the sinonasal mucosa of the individual, before and/or after the administering. In some embodiments, the method further comprises detecting the relative level of Corynebacteria (e.g., *C. tuberculostearicum* and/or *segmentosum*) in a mucosal sample (e.g., sinonasal sample) from the individual and comparing the relative level of *Corynebacterium* in the sample to a control of *Corynebacterium* levels, before and/or after the administering.

Also provided are diagnostic methods, e.g., for determining if an individual has or is at risk of developing sinusitis. In some embodiments, the method of determining whether an individual has or is at risk of developing sinusitis, comprises detecting the relative level of Corynebacteria in a mucosal sample from the individual; comparing the relative level of Corynebacteria in the sample to a control of Corynebacteria levels; and determining that the individual has or is at risk of developing sinusitis where the relative level of Corynebacteria in the sample is higher than the control, wherein the control is a non-sinusitis control, or in the range of the control, wherein the control is a sinusitis-positive control. In some embodiments, the mucosal sample is from the maxillary sinus of the individual. In some embodiments, the mucosal sample is from the ethmoid, frontal, or sphenoid sinus of the individual. In some embodiments, the Corynebacteria is *Corynebacterium tuberculostearicum*.

In some embodiments, the method of determining whether an individual has or is at risk of developing sinusitis, comprises detecting the relative level of at least one bacteria from Table X (e.g., a LAB species, e.g., *L. sakei*) in a mucosal sample from the individual; comparing the relative level of the at least one bacteria from Table X to a control of the level for the at least one bacteria; and determining that the individual has or is at risk of developing sinusitis where the relative level of the at least one bacteria from Table X in the sample is lower than the control, wherein the control is a non-sinusitis control, or in the range of the control, wherein the control is a sinusitis-positive control. In some embodiments, the mucosal sample is from the maxillary sinus of the individual. In some embodiments, the mucosal sample is from the ethmoid, frontal, or sphenoid sinus of the individual. In some embodiments, the at least one bacteria is a LAB species, e.g., a *Lactobacillus* species.

In some embodiments, such methods further obtaining a mucosal sample from the sinonasal mucosa, e.g., the maxillary sinus, of the individual before detecting. In some embodiments, a mucosal sample is taken from the ethmoid, frontal, or sphenoid sinus. In some embodiments, the method is used to confirm a diagnosis of sinusitis using an alternative method, e.g., detection of elevated Muc5A expression or mucosal inflammation, or a higher than normal SNOT-20 score.

In some embodiments, such methods further comprise administering a sinusitis therapeutic agent to the individual based on a determination that the individual has or is at risk of developing sinusitis. In some embodiments, the sinusitis therapeutic is a pharmaceutical composition comprising at least one bacteria listed in Table X. In some embodiments, the pharmaceutical composition comprises at least 2, 3, 4, 5, 6, 7, 8, 9, 10, 20, 30, 40, 50 or more bacteria listed in Table X. In some embodiments, the pharmaceutical composition comprises a Lactic Acid Bacterial (LAB) species, e.g., a *Lactobacillus* species such as *L. sakei*.

BRIEF DESCRIPTION OF THE DRAWINGS

FIG. 2D: Hierarchal cluster analysis demonstrates that the majority of healthy individuals cluster into a group distinct from CRS patients, indicating that sinus microbiome composition of healthy individuals is distinct form that of CRS patients. A heat-plot of sinus symptom severity (based on SNOT-20 scores) demonstrates that altered sinus microbiome composition is related to sinus health status.

FIG. 6A: PAS stained histological sections of murine sinuses representative of animals in each treatment group treated with a combination of antibiotic and *C. tuberculostearicum*. Panel i-iv. Triplicate views of maxillary sinuses from 2 mice per treatment group were used to determine physiology (representative images are shown). Mice treated with a combination of antibiotic and *C. tuberculostearicum* show significantly increased goblet cell hyperplasia (indicated by arrows) and mucin hypersecretion compared to other treatment groups (panel iii). FIG. 6B: Goblet cell enumeration illustrates that, compared to other treatment groups, animals treated with a combination of antibiotic and *C. tuberculostearicum* exhibit significant increases in goblet cell number per μm of epithelium.

FIG. 8A: PAS stained histological sections of murine sinuses representative of animals in each treatment group at 60× magnification (panel i-v). Animals treated with a combination of antibiotic and *L. sakei* (panel iv) exhibit epithelial physiology comparable to untreated or antibiotic treated controls (panels i and ii), while animals treated with a combination of antibiotic and *C. tuberculostearicum* exhibit goblet cell hyperplasia (indicated by arrows) and mucin hypersecretion. Panel v demonstrates that mice treated with antibiotics prior to co-instillation of *C. tuberculostearicum* and *L. sakei* exhibit epithelial physiology comparable to control animals, indicating that *L. sakei* is protective against the pathogenic effects of *C. tuberculostearicum*. Triplicate views of maxillary sinuses from 2 mice per treatment group were used to determine physiology (representative images are shown). FIG. 8B: Enumeration of goblet cells per μm of epithelium confirms that hyperplasia is associated with a high abundance of *C. tuberculostearicum* in the sinuses. Instillation of *L. sakei* does not induce hyperplasia, and co-instillation of *L. sakei* with *C. tuberculostearicum* actually prevents the pathological response to *C. tuberculostearicum*.

DETAILED DESCRIPTION OF THE INVENTION

I. Introduction

Figure 1:
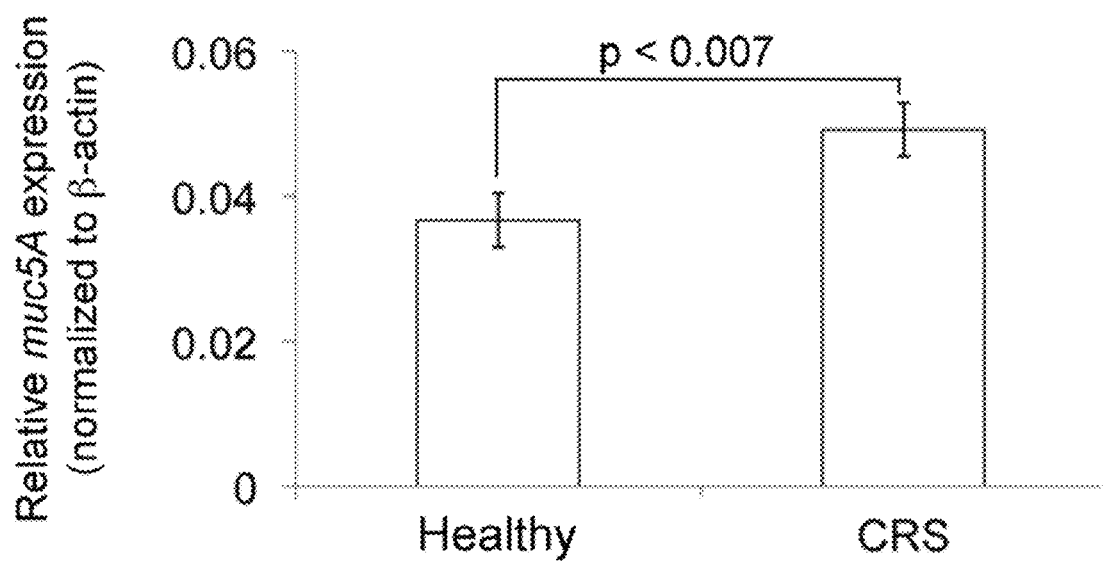
FIG. 1. Muc5A mRNA expression (normalized to β-actin) is significantly increased in CRS patient samples compared to healthy subjects.

Persistent mucosal inflammation and microbial infection are characteristic of Chronic Rhinosinusitis (CRS). The relationship between sinus microbiota composition and CRS is unknown. The present disclosure describes comparative microbiome profiling of a cohort of CRS patients and healthy subjects, demonstrating that the sinus microbiota of CRS patients exhibit significantly reduced bacterial diversity. Characteristic of this community collapse is the depletion of multiple, phylogenetically distinct Lactic Acid Bacteria and the concomitant increase in relative abundance of Corynebacteria, in particular, *C. tuberculostearicum*. The conditions of the human cohort were reproduced in a murine model, and confirmed the pathogenic potential of *C. tuberculostearicum*, as well as the benefit of a diverse, properly composed mucosal microbiota to protect against *C. tuberculostearicum*. Moreover, the results show that *Lactobacillus sakei*, identified from comparative microbiome analyses as protective, affords defense against *C. tuberculostearicum* sinus infection, even in the context of a depleted sinus bacterial community. The results demonstrate that sinus mucosal health depends on the local composition of resident microbiota, identifies a novel sinusitis associated pathogen, and a probiotic therapy for sinusitis.

Human health is dependent on the diverse microbial assemblages that inhabit discrete host niches, particularly mucosal-associated surfaces. To date, culture-based approaches to characterize the etiological agent of CRS have provided a reductionist and somewhat discordant view of the microbiology associated with this disease.

The culture-independent approaches described herein allow the diversity of microbiomes in specific host sites to be better characterized (19-24), including compositional and functional changes in disease states (25), and microbes highly correlated with symptom severity (20) or immune responses (26). The present results show that the composition of the resident microbiota in a given niche can strongly influence the behavior of specific species, particularly a pathogen.

A clear signal emerged from the present results demonstrating that the sinus microbiota of CRS patient cohort were characterized by both grossly depleted communities and a significant increase in relative abundance of *C. tuberculostearicum*. Though phylogenetically its closest bacterial relatives include *Mycobacteria* and *Nocardia*, genera synonymous with pathogenesis, *C. tuberculostearicum* is customarily considered an innocuous member of the healthy skin microbiota, and an unlikely etiological agent of CRS. The presently described murine model of sinusitis confirmed both the pathogenic potential of *C. tuberculostearicum* and that its impact on sinus epithelial responses was significantly enhanced in the absence of a replete sinus microbiota. Demonstration that a bacterial species that commonly inhabits human skin, represents an etiological agent of CRS illustrates why the etiology of CRS, and likely other chronic inflammatory diseases has been so difficult to define.

The role of the microbiome, LAB species in particular, in modulating the impact of *C. tuberculostearicum* on sinus mucosal responses likely explains why it was not previously considered a pathogen. This phenomenon may also explain why, despite detection of known pathogens in the healthy subject sinus microbiota, these subjects exhibit no symptomology and, more broadly, provide an explanation as to why seemingly similar patients, exhibiting comparable quantities of known pathogenic species, may exhibit dramatically different clinical outcomes.

One advantage to the present comparative study design is the ability to identify those species associated with healthy sinuses that provide mucosal protection. The murine sinusitis model provided an opportunity to determine whether such species may afford protection against the pathophysiology induced by a combination of depleted microbiota and *C. tuberculostearicum*. The results demonstrate that *L. sakei* represents a novel probiotic therapeutic for the treatment of sinusitis sub-types, including CRS. Several members of the Lactobacillaceae, including *L. sakei*, as well as other LABs and lactic acid producing members of the Firmicutes were significantly depleted in CRS maxillary sinus. The observation indicates that these species (e.g., through bacteriocin or lactic acid production (30, 31)) can out-compete pathogenic species, shape the sinus mucosal microbiota, and protect this niche from pathogen overgrowth.

The present results also have significant implications for the excessive use of antimicrobials, which contribute to microbiota depletion, in the treatment of viral sinusitis and other upper respiratory infections. The data suggest that microbial supplementation during periods of acute sinusitis with one or a combination of presently identified species would be more appropriate.

II. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier ($4^{th}$ ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "colonize" in the context of the present disclosure refers to microbial growth and expansion. For example, a population of bacteria can be said to colonize an environment if it survives in the environment through at least one round of cell division.

The term "bacterial load" refers to a measure of the total number of bacteria in a given environment, e.g., an airway mucosal surface. The bacterial load is typically expressed as colony forming units (CFU) per ml, per gram of sample or tissue, or per surface area.

The term "microbiome" refers to the community of microbes and environmental interactions in a defined environment. The microbiome also includes the genetic makeup of the microbes. Mucosal surfaces are examples of microbiomes in animals, e.g., the gut, airways, sinus, vagina, oral cavity, etc. Skin, and particular skin areas, comprise additional microbiomes. The term is derived from the term "biome" which can be used synonymously with ecosystem to refer to a larger scale environment and its inhabitants.

The term "improving the sinus microbiota" refers to increasing microbial diversity, increasing the relative amount of beneficial bacteria (e.g., bacteria listed in Table X), or reducing the relative amount of bacteria with high levels in sinusitis patients (e.g., Corynebacteria).

Microbial diversity refers to the range of different species or strains present in a sample. The sample can be highly diverse, with a comparatively wide range of taxa, or lacking in diversity, e.g., with comparatively few taxa represented compared to a normal control. Microbial diversity can be expressed in general comparative terms (e.g., more or less diverse, compared to a normal, healthy control). Microbial diversity can also be expressed in absolute numbers or ranges of numbers, e.g., more than 1000 species or strains, or 500-100, 50-100 or, 25-50 species or strains, etc. in a given environment.

The amount of a particular strain or species of bacteria can be expressed in absolute numbers or ranges of numbers, e.g., $10^6$ or $10^6$-$10^7$ *Lactobacillus* in a sample, or in a given volume. The amount can also be expressed in terms of colony forming units, or absorbance, depending on the assay used for bacterial detection, as will be appreciated by one of skill. The amount can also be expressed in comparative terms, e.g., compared to a control. The relative level of a given strain or species refers to the amount relative to other strains or species within the sample. For example, a high relative level of a Corynebacterial strain indicates that the amount of Corynebacterial strain, as a percentage of total microbes, is higher than that of a normal control. This can be due to depletion of other species in the microbiome, or because of high levels of Corynebacteria.

"Lactic acid bacteria" (LAB) refers to species that fall into the order of Gram-positive Lactobacillalese. LAB genera include: *Lactobacillus, Leuconostoc, Pediococcus, Lactococcus*, and *Streptococcus*, as well as *Aerococcus, Carnobacterium, Enterococcus*, and *Tetragenococcus*.

A "control" sample or value refers to a sample that serves as a reference, usually a known reference, for comparison to a test sample. For example, a test sample can be taken from a patient suspected of having sinusitis and compared to samples from a known sinusitis patient (positive or disease control) or a known normal (negative, non-sinusitis, non-disease, or healthy control) individual. A control can also represent an average range or value gathered from a population of similar individuals, e.g., sinusitis patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters.

One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Subject," "patient," "individual" and like terms are used interchangeably and refer to, except where indicated, humans and non-human animals. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc.

The term "in the range of the control" refers to a value that falls within the range of control values for a given control condition. Where one value is given as a control, "in the range of the control" refers to a value that is not statistically different from the control as determined by one of skill in the art. For example, within the range of the control can be ±5%, 10%, 20%, or within 0.5-fold, 1-fold, or 2-fold difference from a control value at a given condition. One of skill will understand that corrective calculations can be made, e.g., to account for age, severity of condition, antibiotic use, etc.

As used herein, the term "pharmaceutically acceptable" is used synonymously with physiologically acceptable and pharmacologically acceptable with respect to, e.g., a pharmaceutical composition. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose will generally refer to the amount of probiotic, antibiotic or anti-inflammatory agent. Dosage can also be expressed in terms of bacterial concentration. The dose will vary depending on a number of factors, including frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical, and depends on the route of administration. For example, a dosage form can be in a liquid form for nebulization, e.g., for inhalants, in a tablet or liquid, e.g., for oral delivery, or a saline solution, e.g., for injection.

As used herein, the terms "treat" and "prevent" are not intended to be absolute terms. Treatment can refer to any delay in onset, reduction in the frequency or severity of symptoms, amelioration of symptoms, improvement in patient comfort and/or respiratory function, etc. The effect of treatment can be compared to an individual or pool of individuals not receiving a given treatment, or to the same patient prior to, or after cessation of, treatment.

The term "prevent" refers to a decrease in the occurrence of sinusitis symptoms in a patient. As indicated above, the prevention may be complete (no detectable symptoms) or partial, such that fewer symptoms are observed than would likely occur absent treatment.

The terms "effective amount" and "therapeutically effective amount," refer to that amount of a therapeutic agent sufficient to ameliorate the target disorder. For example, for a given disease parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The term "diagnosis" refers to a relative probability that a disease is present in the subject. Similarly, the term "prognosis" refers to a relative probability that a certain future outcome may occur in the subject. The terms are not intended to be absolute, as will be appreciated by one of skill in the field of medical diagnostics.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The terms "label," "tag," "detectable moiety," etc. refer to compositions or components that are detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, *Bioconjugate Techniques* 1996, Academic Press, Inc., San Diego.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA). One of skill in the art will appreciate that specific hybridization between nucleotides usually relies on Watson-Crick pair bonding between complementary nucleotide sequences.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) *Science* 767-773; Johnston (1998) *Curr. Biol.* 8: R171-R174; Schummer (1997) *Biotechniques* 23: 1087-1092; Kern (1997) *Biotechniques* 23: 120-124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived. Such modifications are specifically covered by reference to the individual probes described herein.

The term "antibody" refers to a polypeptide structure, e.g., an immunoglobulin, conjugate, or fragment thereof that retains antigen binding activity, e.g., for a bacterial antigen. The term includes but is not limited to polyclonal or monoclonal antibodies of the isotype classes IgA, IgD, IgE, IgG, and IgM, derived from human or other mammalian cells, including natural or genetically modified forms such as humanized, human, single-chain, chimeric, synthetic, recombinant, hybrid, mutated, grafted, and in vitro generated antibodies. The term encompases conjugates, including but not limited to fusion proteins containing an immunoglobulin moiety (e.g., chimeric or bispecific antibodies or scFv's), and fragments, such as Fab, F(ab')2, Fv, scFv, Fd, dAb and other compositions.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. Typically, the "variable region" contains the antigen-binding region of the antibody (or its functional equivalent) and is most critical in specificity and affinity of binding. See Paul, *Fundamental Immunology* (2003). The terms variable light chain ($V_L$) and variable heavy chain ($V_H$) refer to these light and heavy chains respectively.

Antibodies can exist as intact immunoglobulins or as any of a number of well-characterized fragments produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The terms "antigen," "immunogen," "antibody target," "target analyte," and like terms are used herein to refer to a molecule, compound, or complex that is recognized by an antibody, i.e., can be specifically bound by the antibody. The term can refer to any molecule that can be specifically recognized by an antibody, e.g., a polypeptide, polynucleotide, carbohydrate, lipid, chemical moiety, or combinations thereof (e.g., phosphorylated or glycosylated polypeptides, etc.). One of skill will understand that the term does not indicate that the molecule is immunogenic in every context, but simply indicates that it can be targeted by an antibody. Examples of target antigens in the context of the present disclosure include bacterial antigens (e.g., from *C. tuberculostearicum*, *L. sakei*, or an LAB species) and disease-associated antigens, e.g., Muc5A.

Antibodies bind to an "epitope" on an antigen. The epitope is the localized site on the antigen that is recognized and bound by the antibody. Epitopes can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures.

III. Diagnostic Methods

The present results reveal that sinusitis patients have greatly reduced microbial diversity in the sinonasal environment (e.g., maxillary sinus). In addition, Corynebacterial species (e.g., *C. tuberculostearicum* and *segmentosum*) are present at a higher level than in normal healthy sinus mucosa, and correlate strongly with symptom severity. Sinusitis can also be diagnosed, e.g., by detecting mucin levels, mucosal inflammation, or with self-reporting of sinus inflammation symptoms. Diagnostic methods can be used alone or in any combination.

Patients can thus be selected for therapy based on determination of microbial diversity, reduced levels of beneficial probiotic species (e.g., those listed in Table X, Lactic Acid Bacteria, or *L. sakei* in particular), or elevated levels of Corynebacteria. Anatomical characterization, such as characterization of the sinus mucosal lining, can be accomplished using standard imaging techniques. Bacteria can be detected using nucleic acid techniques as described herein (e.g., arrays, hybridization, or PCR), using sequences complementary to species- or order-specific nucleic acid sequences. Antibodies specific for particular bacterial species can also be utilized.

Methods of obtaining a mucosal sample from an individual are known in the art. Such methods include swabbing or brushing the sinonasal mucosa, e.g., using anesthetic or endoscopic methods if necessary. In some cases, a mucosal biopsy is taken. Samples can also be obtained using a nasal lavage or spray in sufficient volume to obtain sample from the appropriate location. Comparison of various sample gathering techniques is described, e.g., in Roediger et al. (2010) *Am J Rhinol Allergy* 24:263.

A diagnostic agent specific for the microbes described herein can include any label as known in the art, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal. Detectable signals include, but are not limited to, fluorescent, luminescent, gamma-emitting, radioactive, optical, absorptive, etc. The terms "detectable agent," "detectable moiety," "label," "imaging agent," and like terms are used synonymously herein.

A radioisotope can be incorporated into the diagnostic agents described herein and can include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y.

In some embodiments, the diagnostic agent can be associated with a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Secondary binding ligands include, e.g., biotin and avidin or streptavidin compounds as known in the art.

In some embodiments, the diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives.

IV. Methods and Compositions for Administration

Provided herein are methods of improving sinus microbiota (e.g., increasing microbial diversity or reducing the relative population of pathogenic species) in an individual comprising administering a pharmaceutical composition comprising a beneficial microbe, e.g., from Table X, to the individual. Typically, the composition is administered nasally, trans-nasally, or to the sinuses, e.g., using an aerosol, spray, irrigation, or nasal drops. Such methods can be used to treat an individual diagnosed with sinusitis.

A pharmaceutical composition comprising a beneficial microbe described herein can be administered, alone or in combination with other suitable components, using an aerosol formulations ("nebulized") to be administered via inhalation. Aerosol formulations can be placed into pressurized acceptable propellants, such as dichlorodifluoromethane, propane, nitrogen, etc.

Compositions for administration typically comprises at least one probiotic microbe, e.g., as identified in Table X, in a pharmaceutically acceptable carrier, e.g., an aqueous carrier. A variety of aqueous carriers can be used, e.g., buffered saline. These solutions are generally free of undesirable matter, e.g., contaminating species. The compositions can contain pharmaceutically acceptable auxiliary substances as required to approximate physiological conditions such as pH adjusting and buffering agents, for example, sodium acetate, sodium chloride, potassium chloride, calcium chloride, sodium lactate, etc. The concentration of active agent in these formulations can vary widely, and will be selected primarily based on fluid volumes, viscosities, body weight and the like in accordance with the particular mode of administration selected and the patient's needs.

The formulation may also provide additional active compounds, including, e.g., antibiotic or anti-inflammatory agents. Combination therapies contemplate coadministration, using separate formulations or a single pharmaceutical formulation, and consecutive administration in either order.

The active ingredients can be prepared as sustained-release preparations (e.g., semi-permeable matrices of solid hydrophobic polymers (e.g., polyesters, hydrogels (for example, poly (2-hydroxyethyl-methacrylate), or poly (vinylalcohol)), polylactides. The probiotic formulations described herein can also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

Methods for preparing therapeutic compositions will be known to those skilled in the art and are described in more detail in such publications as Remington's Pharmaceutical Science, 15th ed., Mack Publishing Company, Easton, Pa. (1980).

The compositions can be administered for therapeutic or prophylactic treatments. In therapeutic applications, compositions are administered to a patient suffering from a disease (e.g., sinusitis) in an effective dose. Amounts effective for this use will depend upon the route of administration, the severity of the condition, and the general state of the patient's health. Single or multiple administrations of the compositions may be administered depending on the dosage and frequency as required and tolerated by the patient. The presently described compositions can be administered to humans and other animals. Thus the methods are applicable to both human therapy and veterinary applications.

To determine a therapeutically effective dose, e.g. a colonizing dose of a probiotic composition, a relatively low dose of the composition can be initially administered to the individual, and the dose can be incrementally increased until the condition of the individual, e.g., the sinus environment, begins to improve (e.g., reduced mucin secretion or goblet cell hyperplasia, or increased microbial diversity). In some cases, however, the initial dose is relatively high to establish a colonizing population in a patient experiencing acute symptoms. One of skill will appreciate that a number of variables must be considered when determining a therapeutically effective dose. The dose administered to a patient should be sufficient to effect a beneficial therapeutic response in the patient over time. The size of the dose also will be determined by the existence, nature, and extent of any adverse side-effects that accompany the administration of a particular composition (or combination therapy) in a particular patient.

V. Kits

Further provided are kits for detecting at least one sinusitis associated bacterial taxa (i.e., bacteria with high levels correlating with sinusitis, or bacteria are associated with the absence of sinusitis, such as the bacteria in Table X). The kit can optionally include written instructions, reference to an internet site, or electronic instructions (e.g., on a CD-ROM or DVD). In some embodiments, kits of the invention will include a case or container for holding the reagents in the kit, which can be included separately or in combination. In some embodiments, the kit includes brushes, swabs, or other sample gathering devices for obtaining a sinonasal sample from an individual, e.g., from the maxillary, ethmoid, frontal, and/or sphenoid sinus. The kit can further comprise sample containers for holding and processing samples, and for detection of sinonasal microbes in the sample.

In some embodiments, the kit includes an array, the array comprising probes or other agents capable of specific detection of at least one sinusitis associated bacterial taxa. For example, the array can comprise probes that specifically hybridize to nucleotide sequences from the at least one sinusitis associated bacteria, e.g., polynucleotide or oligonucleotide probes. In some embodiments, the array comprises components (e.g., antibody fragments) that specifically detect non-nucleic acid markers from the at least one sinusitis associated bacteria. In some embodiments, the array can specifically detect at least 4, 5, 10, 12, 15, 20, 50, 80, 100, or all of the sinusitis associated bacteria, e.g., Corynebacteria or those listed in Table X. In some embodiments, the kit further includes reagents (buffers, secondary detection agents, etc.) required for running the detection reaction.

In some embodiments, the kit will include PCR reagents and primers for detecting at least one of the bacteria disclosed in Table X, or at least one Corynebacterial species. The kit can thus include a polymerase, nucleotide monomers, buffer stocks, and optionally an interchalating fluorescent dye. In some embodiments, the kit can include PCR primers for at least 4, 5, 10, 12, 15, 20, 50, 60, or all of the sinusitis associated bacteria, e.g., Corynebacteria or those listed in Table X.

In some embodiments, the kit can include PCR primers for detecting a polynucleotide from at least one sinusitis associated bacteria, e.g., Corynebacteria (e.g., *tuberculostearicum* or *segmentosum*), or at least one bacteria listed in Table X. The primers can be designed to amplify more than one species or strain from a bacterial taxa, e.g., more than one Corynebacteria or *Lactobacillus* strain.

In some embodiments, the kit will include a positive control for the at least one sinusitis associated bacteria (e.g., an isolated sample of the bacteria). In some embodiments, the kit will include a negative control for the at least one sinusitis associated bacteria (e.g., a blank, or an unrelated bacterial sample).

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, Accession or ID numbers, and websites cited herein are hereby incorporated by reference in their entirety for all purposes.

VI. Examples

A. Materials and Methods

Patient Sample Collection.

Patient and disease stratification was performed based on recent clinical history, nasal endoscopy, CT sinus review, and a validated quality-of-life instrument, the disease-specific Sinonasal Outcome Test survey [SNOT-20; (38)]. Sinus brushings were obtained during functional endoscopic sinus surgery (FESS) of CRS patients, or surgery for non-CRS complaints, e.g., obstructive sleep apnea or post-traumatic malocclusion, in healthy subjects. Endoscopically-guided brush samples of mucosal surfaces of the lateral, central, and medial portions of the maxillary sinus were obtained and pooled together in 1 ml of RNALater for analysis. Samples were placed at 4° C. for 24 hours prior to storage at −80° C. until processed.

DNA Extraction and PhyloChip Analysis.

Mucosal brushings were transferred to Lysis Matrix B (MP Biomedicals, OH) tubes containing 600 ul RLT buffer (Qiagen, CA). Samples were subjected to 30 seconds of bead beating at 5.5 m/second followed by centrifugation for one minute at 2000 rpm. Supernatant was transferred to the AllPrepDNA spin column and nucleic acid purification (DNA and RNA) was carried out according to the manufacturer's instructions (Qiagen, CA). Nucleic acid concentrations were determined using a NanoDrop spectophotometer (Thermo Scientific, DE). PhyloChip analysis was performed as previously described (40) using 250 ng of purified pooled 16S rRNA amplicon per sample generated using 27F and 1492R universal primers (41). Data sets were conservatively filtered as previously described (40). Probe-set fluorescence intensity was normalized and log transformed prior to analysis using packages in the R statistical environment. Hierarchical cluster analysis (HCA) was performed on a Bray-Curtis dissimilarity matrix generated from PhyloChip fluorescence intensity data using the vegan package as we have previously described (22), followed by average linkage clustering.

A two-tailed Welch's T-test was used to identify taxa that were significantly altered in relative abundance across healthy subject and patient groups and adjusted for false discovery (42) using the q-value package as previously described at the website accessible at cran.r-project.org/web/packages/qvalue/qvalue.pdf. Results with a p-value <0.05 and q-value <0.05, were considered statistically significant. The 16S rRNA sequences of significant taxa were used to construct a neighbor-joining with nearest-neighbor interchange tree using FastTree (43) which was annotated using the Interactive Tree of Life website accessible at itol.embl.de (44).

Murine Sinus Studies.

Female 4-5 week old C57BL6/J mice weighing 16 to 18 g were purchased form Jackson Laboratories (Bar Harbor, Me.) and housed in micro-isolator cages. Animals were permitted to acclimatize for two weeks with food and water ad libitum prior to study. Mice were administered augmentin (amoxicillin/clavulanate) at 100 mg/kg dosage once a day for five days prior to bacterial instillation. Prior to intra-nasal C. tuberculostearicum, L. sakei, or combination of both C. tuberculostericum and L. sakei, inoculations mice were anesthetized by intraperitoneal injection with avertin (250 mg/kg). Inoculation was performed once a day for three days by applying 25 µl of either C. tuberculstearicum suspension ($1.0 \times 10^{11}$ cfu/ml) or L. sakei ($1.0 \times 10^{11}$ cfu/ml) suspension, or combination of both microbes in equal ratios (total $2.0 \times 10^{11}$ cfu/ml), in PBS onto the external nares and inhalation by the animals (see e.g., 45, 46). Mice were monitored for breathing during the entire inoculation process and post inoculation until fully recovered from anesthesia. Twenty-four hours after the final bacterial inoculation, mice were euthanized by $CO_2$ asphyxiation followed by induced pneumothorax. The heads were decapitated and sinuses dissected for histological (n=2 animals per treatment group) and molecular analysis (n=3 animals per treatment group). Dissected sinuses used for molecular analyses were placed in RNAlater (Ambion, TX) and stored at 4° C. until processed the following day in the same manner as described above for human samples.

Sinus Histology.

Sinuses used for histological analysis were fixed overnight in 4% paraformaldehyde, followed by overnight decalcification in Decalcifying solution A (Fisher, CA). Samples were then dehydrated as follows: rinsed with PBS (1 hour), soaked in 30% ethanol (1 hour), 50% ethanol (1 hour), then transferred to 70% ethanol and stored at 4° C. until subsequent preparation. Sinus samples were sectioned to 5 µm thickness and mounted onto glass microscope slides. H&E and PAS staining were performed as previously described (47). PAS-stained sections prepared from four groups of mice (CT–AB–, CT–AB+, CT+AB– and CT+AB–) were imaged at 20× and 60× magnifications, and PAS-positive cells were counted for 3 different sections per mice (2 mice in each group). The number of goblet cells was expressed as the total number of PAS-positive cells per µm length of epithelium. Students t-test was used to calculate p-values, p<0.05 was considered significant.

Q-PCR.

Bacterial burden was determined using extracted DNA (10 ng per sample, triplicate reactions) and universal 16S rRNA Q-PCR primers [338F, 5'-ACTCCTACGGGAGG CAGCAG-3' (41) and 518R 5'-ATTACCGCGGCT-GCTGG-3'(48)]. Quantitec SYBR Green (Qiagen, CA) was used according to manufacturer's instructions. Reaction mixtures (25 µl total) contained 12.5 µl of 2× QuantiTec SYBR green (Qiagen, CA), 2.5 µl each of 3 µM forward and reverse primer, and 6.5 µl $H_2O$. Reactions were amplified using the Mx3000P Real-Time PCR System (Stratagene, CA) and the following cycling conditions: 95° C. for 10 min followed by 40 cycles of 95° C. for 30 sec, 55° C. for 1 min and 72° C. for 30 sec. The data acquisition step was set at 55° C. Corynebacteriumtuberculostearicum abundance was determined by Q-PCR using a pair of primers designed in this study: CT-F: 5'-GAACGGAAAGGCCCTGCTTGCA-3' and CT-R 5'-GGCTCCTATCCGGTAT TAGACC-3'; Lactobacillus sakei abundance was determined using the primer pair: LS-F: 5'-GGTAAAGGCTCACCAAGACCGTGAT-3' and LS-R: 5'TCACGCGGCGTTGCTCCATC-3'. Reaction mixtures (25 µl total) contained 10 ng of total DNA, 12.5 µl of 2× QuantiTec SYBR green (Qiagen, CA), 2.5 µl of each primer and 6.5 µl of $H_2O$. Reactions were amplified on the Mx3000P Real-Time PCR System (Stratagene, CA) under the following steps: 95° C. for 10 min followed by 40 cycles of 95° C. for 30 sec, 55° C. for 1 min and 72° C. for 30 sec. The data acquisition step was set at 55° C.

For Muc5A expression analysis, confirmed DNA-free total RNA (1 µg) was reverse transcribed at 42° C. for 50 min in a 20 µl reaction mixture (0.025 oligo-dT, 0.5 mMdNTPs, 5 µl First Strand buffer, 5 mM MgCl2, 0.01 M DTT, and RNAse Out) using 1 µl Superscript II (Invitrogen, CA). cDNA was diluted 1:5 in molecular grade water. Reactions were performed in 96 well plates in a 25 µl final volume containing 12.5 µl of SYBR Green PCR master mix (Qiagen, CA), 2.5 µl of each forward and reverse primer (final concentration 10 µM per primer; Muc5AF 5'-TGTG-GCGGGAAAGACAGC-3' Muc5AR 5'-CCTTCCTATG-GCTTAGCTTCAGC-3'; β-actinF 5'-CACCACACCTTC-TAC AATGAGC TGC-3' and β-actinR 5'-ACACCCTGGATAGCAACGTACATGC-3'), 4 µl of diluted cDNA, and 6 µl of molecular grade water. Reactions were amplified on a Mx3000P Real-Time PCR System under the following conditions: 94° C. for 10 min followed by 40 cycles of 94° C. for 30 sec, 58° C. for 1 min and 72° C. for 30 sec. Students t-test was used to calculate p-values for individual treatment groups, p<0.05 was considered significant.

B. Example 1: Comparative Sinus Microbiota Analysis

Maxillary sinus samples from 20 subjects (10 CRS and 10 healthy individuals) were used for this study. Patient details are provided in Table 1. Mucin hyper-secretion is a hallmark of sinus disease (12, 13). Therefore, to confirm that the CRS patients exhibited a phenotype consistent with disease, Q-PCR analysis of Muc5A gene (encoding mucin primarily secreted from surface epithelium goblet cells in humans (14, 15)) expression was performed. Muc5A was significantly up-regulated in CRS patients compared to healthy control subjects (FIG. 1), thus validating the presence of sinus disease in our CRS cohort. Q-PCR analysis of bacterial burden by total 16S rRNA copy number demonstrated that peri-operative CRS patients and healthy subjects exhibited no significant difference in sinus bacterial burden ($2.19 \times 10^6 \pm 1.09 \times 10^6$ vs $2.86 \times 10^6 \pm 2.34 \times 10^6$ copies of 16S rRNA gene per µg of total DNA in CRS and healthy control subjects respectively; p≤0.53). The result indicates that the sinus niche can support a defined bacterial load, and that microbiota composition and relative taxonomic distribution, rather than absolute number of bacteria present, are related to disease state.

TABLE 1

Patient information.

| Group | Study ID | Gender | Age | SNOT-20 | Antimicrobial treatment Pre-operative | Peri-operative |
|---|---|---|---|---|---|---|
| CRS | CRS-001[a] | M | 54 | 2.75 | None[b] | Cefazolin |
| CRS | CRS-002 | M | 54 | 2.35 | TMP/SMX[c] | Vancomycin |
| CRS | CRS-003[a] | M | 48 | 2.65 | None | AMP/SUL[d] |
| CRS | CRS-004 | M | 33 | 3.60 | None | Cefazolin |
| CRS | CRS-005[a] | M | 56 | 2.65 | Clarithromycin | Cefazolin |
| CRS | CRS-006 | F | 41 | 1.85 | None | Cefazolin |
| CRS | CRS-007 | M | 60 | 3.00 | Clarithromycin | Levofloxacin |
| CRS | CRS-008 | M | 53 | 1.55 | Ciprofloxacin | Cefazolin |
| CRS | CRS-009 | F | 46 | 2.35 | AMO/CLU[e] | Cefazolin |
| Control | CRS-010 | M | 62 | 0.90 | Levofloxacin | Centriaxone |
| CRS | CRS-011 | M | 42 | 3.35 | AMO/CLU | Clindamycin |
| Control | CRS-012[a] | M | 43 | 0.15 | None | Clindamycin |
| Control | CRS-013 | F | 73 | 1.70 | None | Cefazolin |
| Control | CRS-014 | M | 41 | 2.60 | None | Clindamycin |
| Control | CRS-015[a] | M | 39 | 0.00 | None | Clindamycin |
| Control | CRS-016[a] | F | 37 | 2.25 | None | Cefazolin |
| Control | CRS-017 | F | 46 | 0.10 | None | Clindamycin |
| Control | CRS-018 | M | 46 | 2.15 | None | Clindamycin |
| Control | CRS-019 | F | 31 | 0.50 | None | Clindamycin |
| Control | CRS-020 | F | 18 | 0.30 | None | Clindamycin |

[a]Microbiota profiling was not preformed for these subject samples due to insufficient 16S rRNAamplicon;
[b]None, no antibiotics administered;
[c]TMP/SMX, Trimethoprim/Sulfamethoxazole;
[d]AMP/SUL, Ampicillin/Sulbactam;
[e]AMO/CLU, Amoxicillin/clavulanate.

Figure 2A:
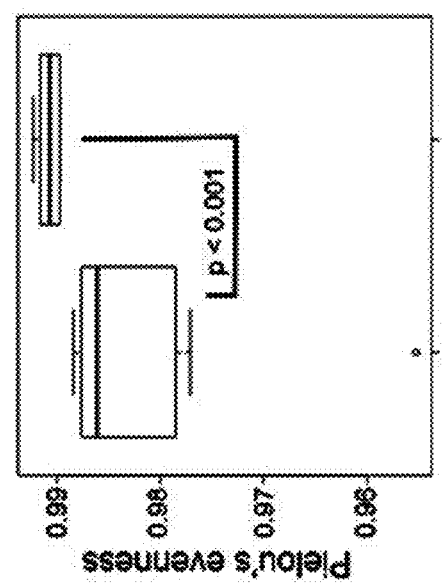
FIGS. 2A-2D. Bacterial community Richness (FIG. 2A), Evenness (FIG. 2B) and Shannon diversity (FIG. 2C) indices are significantly lower in CRS patient sinuses compared with healthy individuals, indicating gross perturbation to the sinus mucosal microbiota in the disease state.
Figure 2B:
Figure 2C:
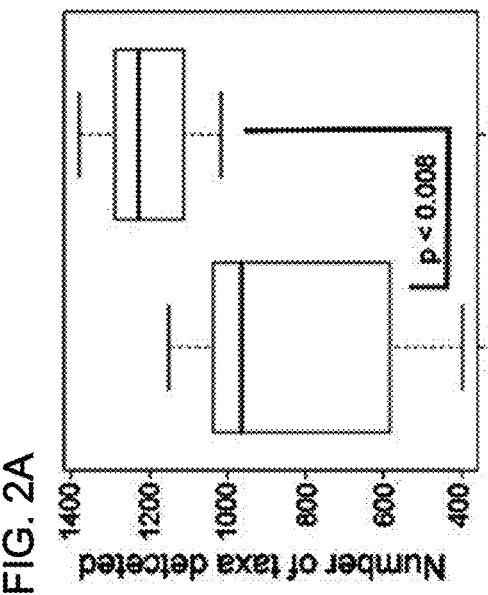

A standardized phylogenetic microarray, the 16S rRNA-PhyloChip was used to profile the presence and relative abundance of approximately 8,500 bacterial taxa, representing broad membership of all known bacterial phyla (Hugenholtz phylogenetic classification). This approach was used in favor of more traditional sequencing approaches to maximize the depth of community coverage. Low abundance microbiome members can contribute considerably to microbiome function (16) and act as keystone species that shape microbial community composition (17). Using this tool, we profiled bacterial communities present in 14 subjects (7 healthy, 7 CRS) with sufficient amplified 16S rRNA product to be analyzed. Comparative analyses of gross bacterial community metrics between the CRS and healthy groups demonstrated that compared to healthy individuals, CRS patients exhibited substantial microbiota perturbation, characterized by significantly reduced bacterial richness ($p \leq 0.005$; number of bacterial types detected; FIG. 2A), evenness ($p \leq 0.04$; relative distribution of bacterial types; FIG. 2B) and diversity ($p \leq 0.01$; metric calculated using richness and evenness indices; FIG. 2C).

Figure 2D:
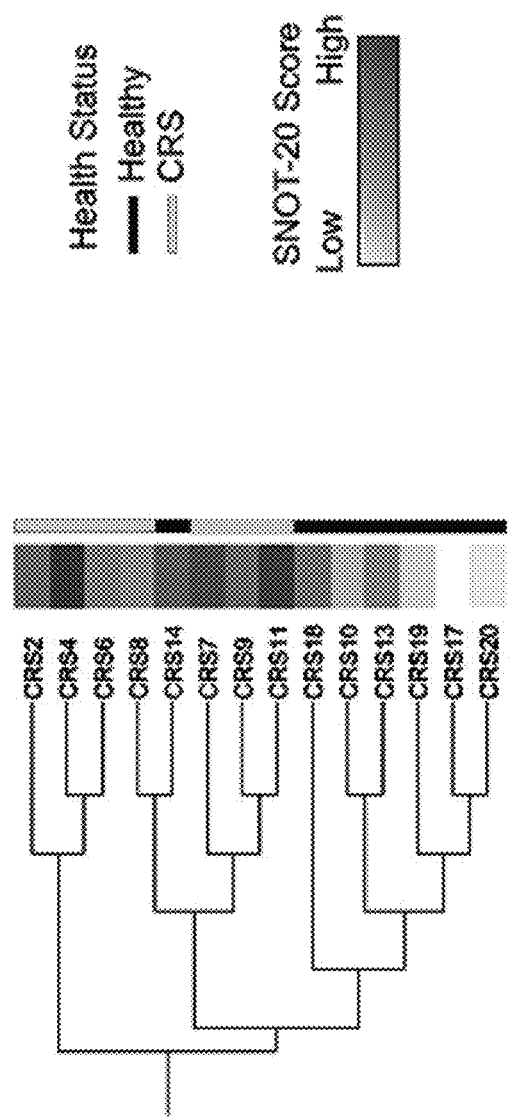

Reduced diversity was further demonstrated by hierarchical cluster analysis which revealed that the majority of healthy subjects clustered in a single tightly-knit group, with bacterial communities compositionally distinct from CRS patients who clustered into two distinct groups (FIG. 2D). Healthy subject CRS 14, clustered with CRS patients, and it was subsequently determined that this individual had historically suffered from chronic nasal allergies. The present analysis thus confirms that the sinus microbiota composition of healthy subjects is distinct from that of CRS patients and, that within the CRS population, discrete sub-groups with distinct microbial community profiles exist.

Antibiotic use was examined, as it influences microbiota composition. All study subjects (CRS and healthy) received prophylactic antibiotics immediately (1 hour) prior to surgery and sample collection according to standard practice. Long-term pre-operative antibiotic use was absent for the majority of healthy subjects, and variable in the CRS patient group (Table 1). Patients with disparate long-term antimicrobial administration histories (e.g. CRS 4, 6 and 2; Group II; Table 1) clustered closely together. Moreover, Group II included two patients who had not received long-term antibiotics, and who exhibited significantly lower ($p<0.006$) sinus community diversity compared to microbiota from patients in Group I. Group I subjects had received long-term prophylactic antibiotic administration, indicating that while antibiotic therapy may contribute, it is not the sole selective pressure defining bacterial community composition and loss of diversity in this niche.

C. Example 2: Taxa Characteristic of Healthy and CRS Sinuses

Results from the Sino-Nasal Outcomes Test (SNOT-20) questionnaire, a metric to score sinus symptomology, confirmed that CRS patients reported significantly higher scores (i.e., more severe sinus symptomology ($p \leq 0.003$)) than healthy controls. The observed microbiota clustering patterns were consistent with patient-reported sinus symptomology, as shown in FIG. 2D). Given this level of independent validation of disease activity, specific community members that differentiated healthy subjects and CRS patients were next characterized at the taxonomic level.

Known pathogenic members of the Pseudomonadaceae, Lachnospiraceae, Ralstoniaceae, Mycobacteriaceae and Helicobacteriaceae were detected in both CRS patients with, and healthy subjects without, sinonasal symptoms. Thus, the mere detection of a suspected or known pathogen in a given niche does not necessarily imply pathogenic activity, indicating that the microbiota composition at a given site may play a large role in defining the activity of community members.

Following correction for false discovery ($p \leq 0.05$, $q \leq 0.05$), a total of 1,482 taxa were detected in significantly lower relative abundance in CRS patient sinuses, underscoring the extent of sinus microbiota collapse in the CRS patient population. A large number of taxa exhibiting the most significant reductions in relative abundance in the CRS patients belonged to the order Lactobacillales and included probiotic species such as Lactobacillus sakei, as well as other phylogenetically distinct lactic acid bacteria (LAB) such as Carnobacterium alterfunditum, Enterococcus mundtii and Pediococcus pentosaceus implicating LAB in maintenance of healthy sinus mucosa. In stark comparison, only Corynebacteria, in particular, Corynebacterium tuberculostearicum, (Taxon ID 1493, str. CIP102346) exhibited a significant increase in abundance in CRS patients (Correlation value: 0.6220027; p≤0.03, q≤0.003). Corynebacterium segmentosum (Taxon ID 1192, str. CIP107068 (CCUG37878)) was also correlated with CRS (Correlation value: 0.5514262; p≤0.05).

Figure 3:
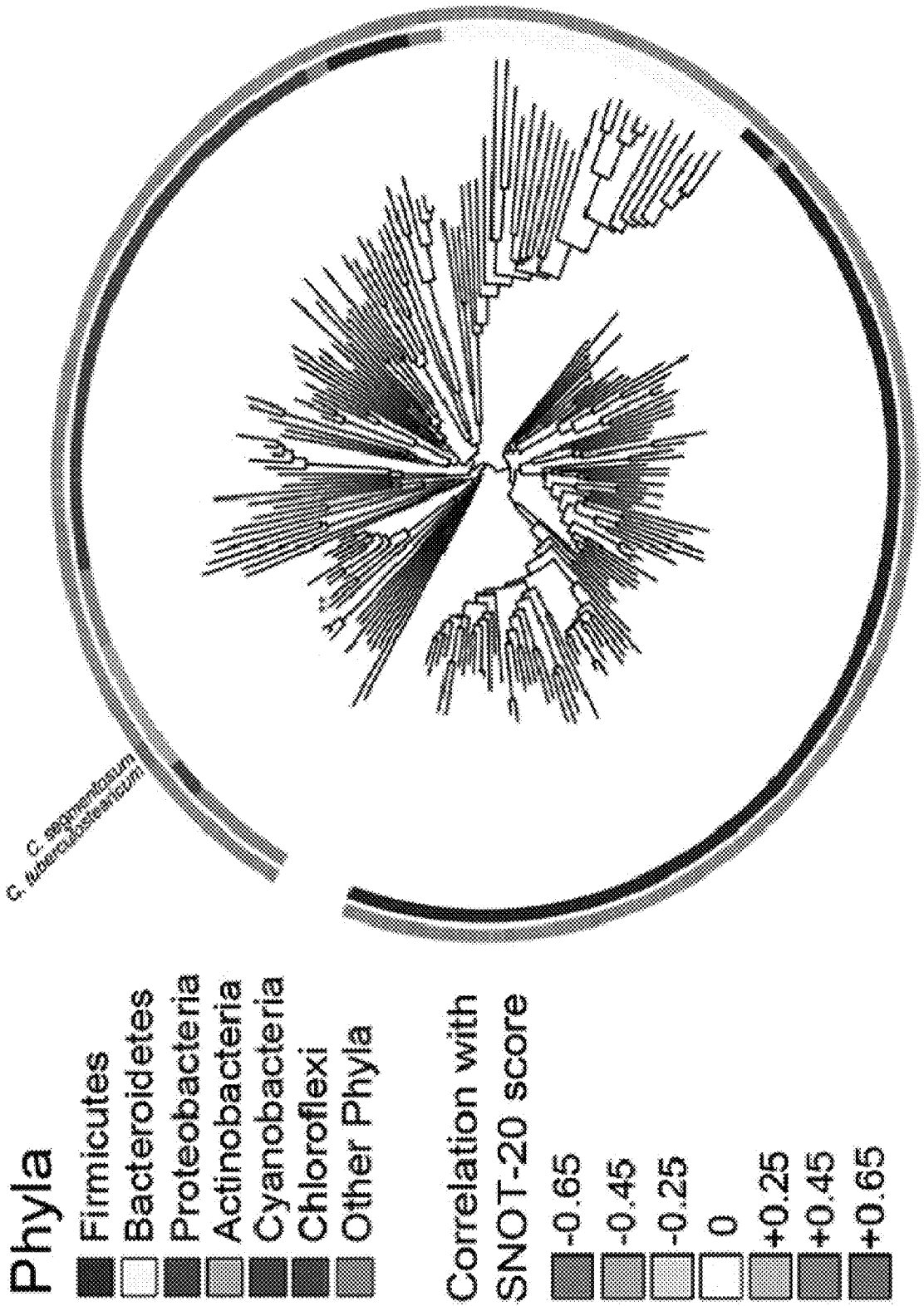
FIG. 3. Phylogenetic tree demonstrating the breadth of bacterial community members exhibiting significant positive or negative correlations with sinus symptom severity (determined by SNOT-20 score). *Corynebacterium tuberculostearicum* and *C. segmentosum* exhibited strong and significant positive correlations with severity of sinus symptomology, implicating them in disease etiology. Other community members illustrated, e.g., in Table X, exhibited significant negative correlations with sinus symptomology. The results indicate that these species maintain sinus mucosal health.

The microbiota data were examined to identify those species that correlated with SNOT-20 symptom severity scores, in order to further confirm the clinical significance of these findings. A large group of 228 taxa were significantly (p<0.05) correlated with lower SNOT-20 scores (indicative of healthy sinuses; FIG. 3; Table X). Amongst these taxa were members of the LAB, e.g., Lactobacilliaceae, Enterococcaceae, Aerococcaceae, and Streptococcaceae, further supporting the idea that these families are protective in healthy sinuses.

Figure 4A:
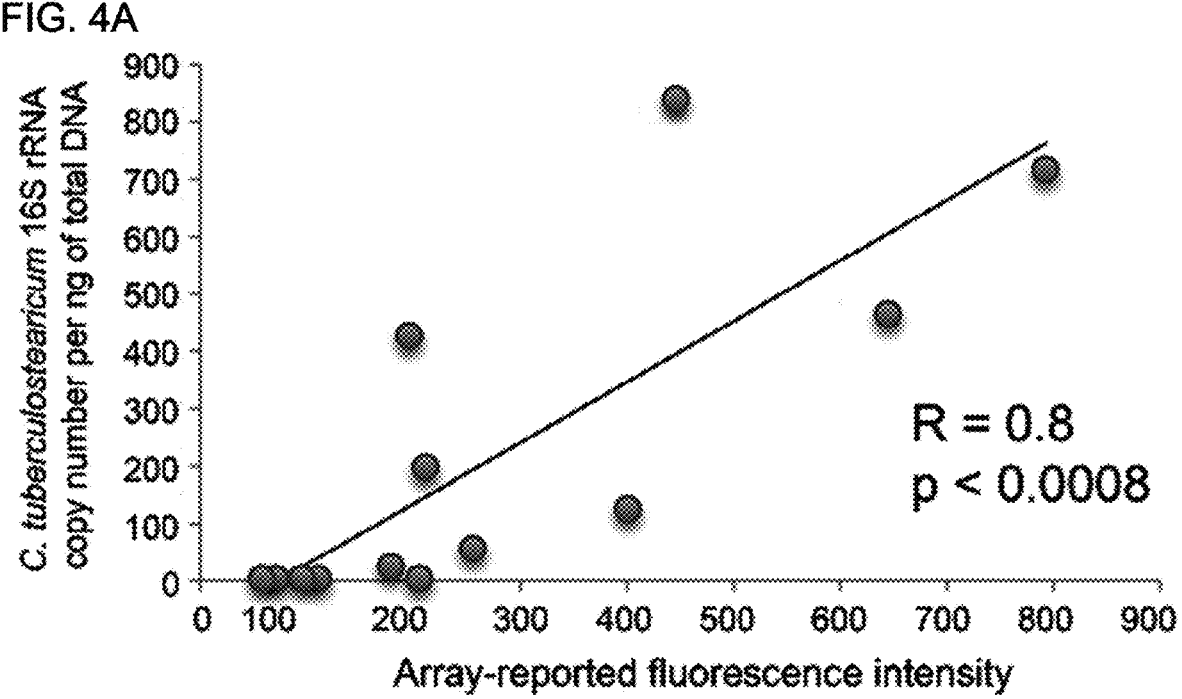
FIGS. 4A-4B. Linear regression of Q-PCR-derived *C. tuberculostearicum* abundance with array reported florescence intensity (FIG. 4A) and SNOT-20 score (FIG. 4B) indicate strong concordance between Q-PCR and array-generated findings and confirm a strong positive relationship between *C. tuberculostearicum* abundance and symptom severity.
Figure 4B:
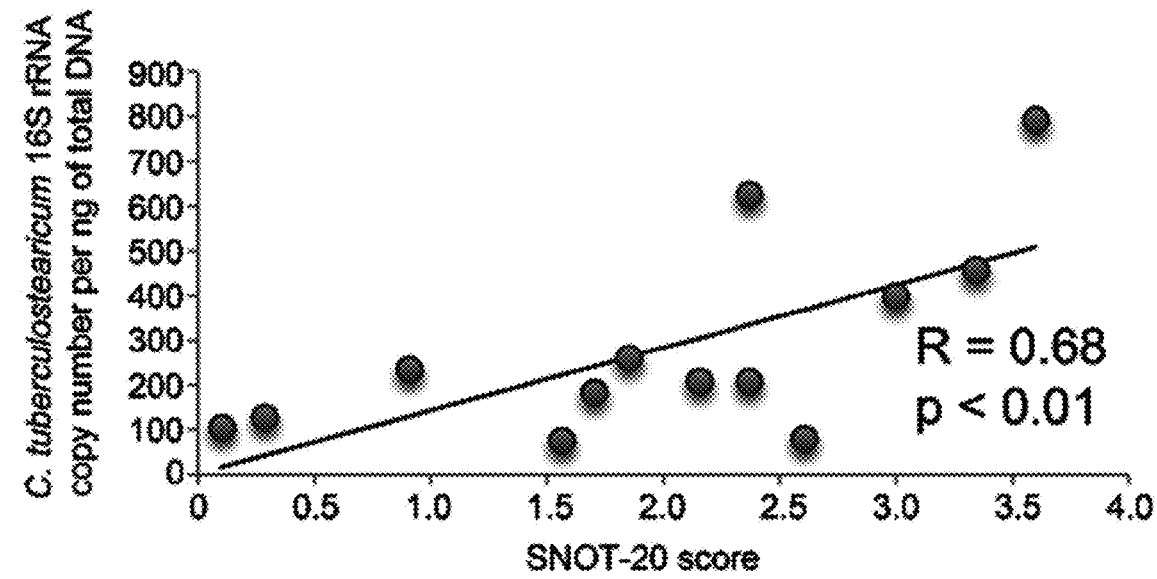

As noted above, the relative abundance of only two bacterial species was positively correlated with increased symptom severity; both belonged to the Corynebacteriaceae, with C. tuberculostearicum most correlated with symptom severity (r=0.62; p≤0.02). Q-PCR analysis was performed using primers designed to specifically amplify C. tuberculostearicum to validate these findings. Linear regression of C. tuberculostearicum Q-PCR-derived copy number against both array-reported fluorescence intensity or against SNOT-20 score demonstrated concordance (r=0.66; p≤0.01 and r=0.68; p≤0.01 respectively). The regression data thus corroborate the array-based findings and confirm a strong relationship between the abundance of this species and sinus symptom severity (FIGS. 4A-4B).

D. Example 3: Murine Model of Sinusitis

To determine whether C. tuberculostearicum, which is typically considered a skin commensal, exhibited any pathogenic potential, a murine model of sinus infection was developed. Goblet cell hyperplasia and mucin hypersecretion were used as indicators of pathology (12), and as the outcome measures to define pathogenic activity in the sinuses. This model is also allows for determination of whether C. tuberculostearicum is influenced by resident microbiota in the sinus cavity.

Figure 5:
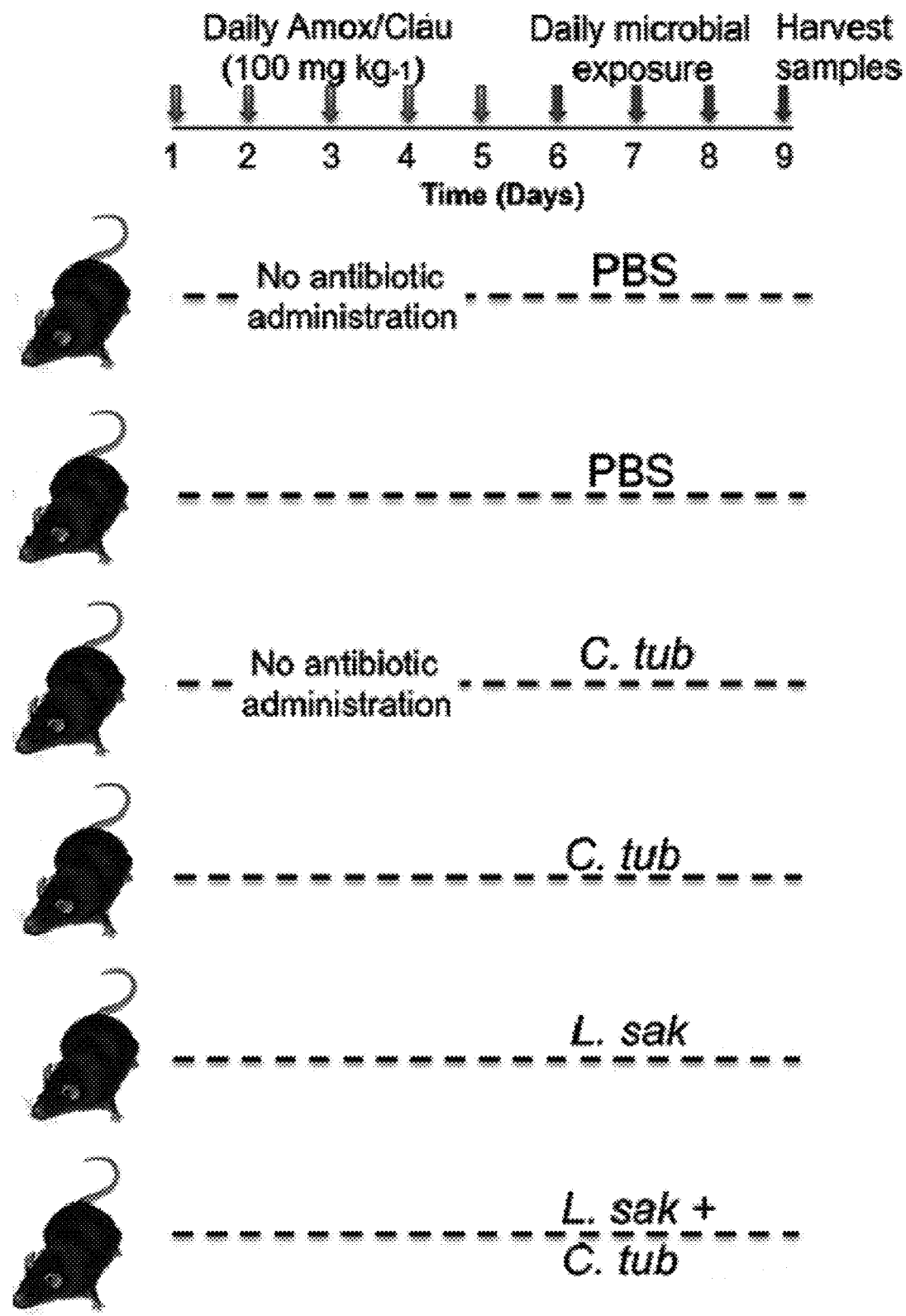
FIG. 5. Murine experimental design. Amox=Amoxicillun; Clau=Clavulanate.

Four groups of mice (n=5 animals per group) representing: i. Untreated control; ii. Antibiotic treated (to elicit microbiome depletion); iii. C. tuberculostearicum (ATCC #35694) inoculated; and iv. Antibiotic treated and C. tuberculostearicum inoculated animals were used (FIG. 5). Q-PCR analyses of total 16S rRNA copy number from the sinuses of these animals confirmed that the burden of bacteria in the antibiotic treated groups was significantly lower (p>0.03) than that of untreated animals. The data confirm acute antimicrobial depletion of bacterial burden and mucosal sinus microbiota diversity in antibiotic-treated groups. Histological examination of the sinus mucosa from each group demonstrated that the untreated control and antibiotic treated animals did not exhibit aberrant epithelial physiology (FIG. 6A, panels i and ii), while instillation of C. tuberculostearicum in the presence of a replete sinus microbiota elicited a modest increase in the number of mucin-secreting goblet cells (FIG. 6A, panel iii).

Figure 6A:
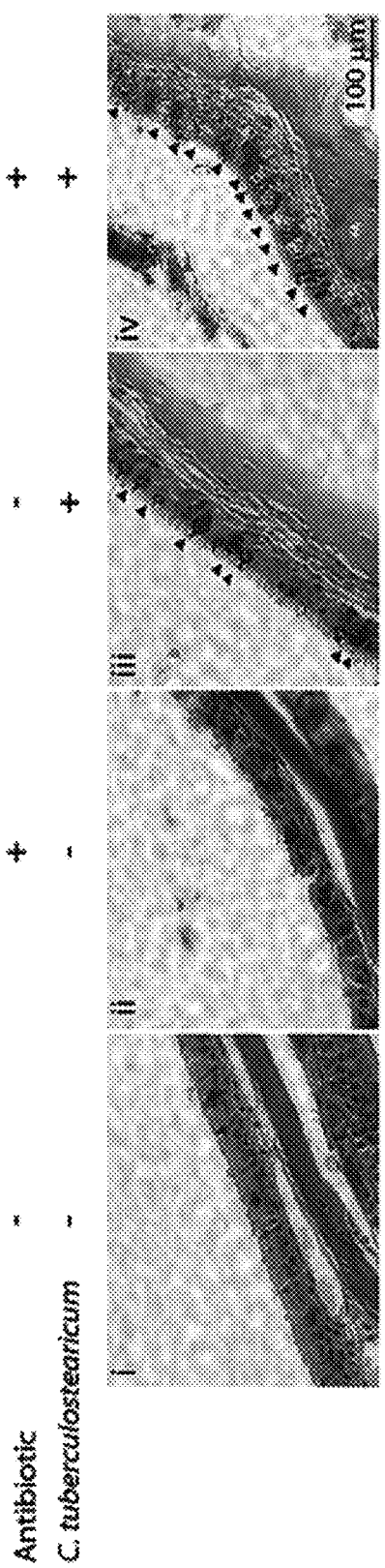
FIGS. 6A-6B.
Figure 6B:
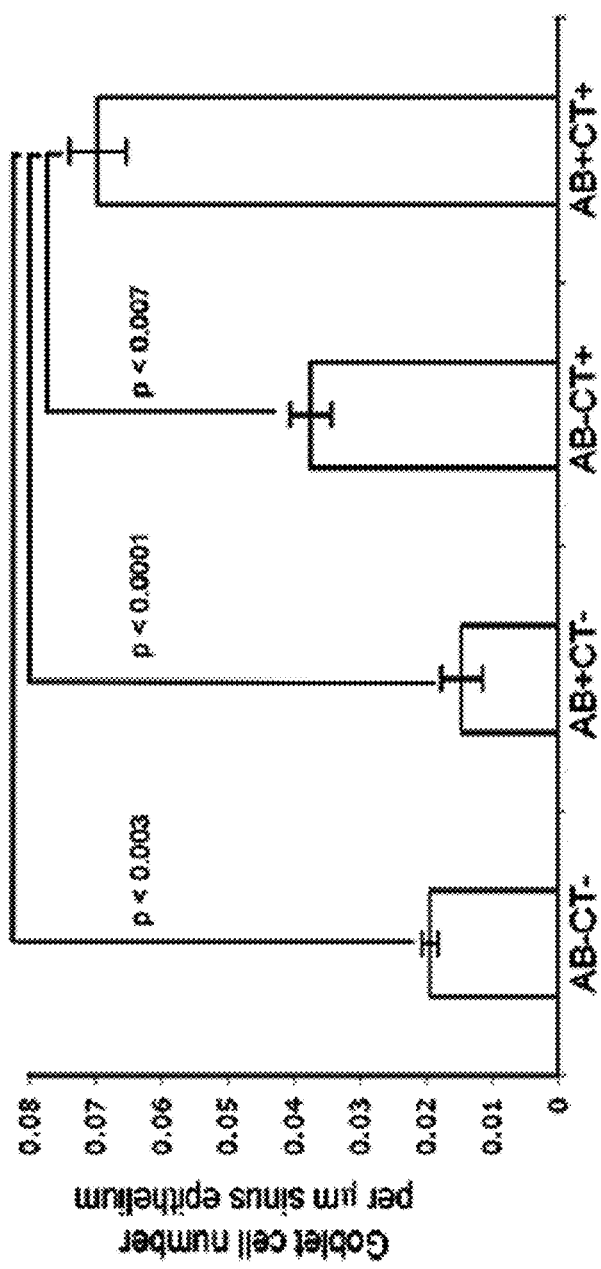

Animals treated with both antimicrobial and C. tuberculostearicum exhibited profound goblet cell hyperplasia, (FIG. 6A, panel iv; FIG. 6B and Table 2), significantly greater than that observed in any other group. Since mucin hypersecretion is a hallmark of respiratory infection (18) and chronic sinusitis (12, 13), these data confirm that C. tuberculostearicum is capable of inducing a characteristic response to pathogenic microbes and that this response is significantly augmented under conditions of depleted sinus microbiota.

TABLE 2 p-values for goblet cell number per µm of epithelial cell surface compared across mouse treatment groups (FIGS. 6A-6B).

| | AB− CT− | AB+ CT− | AB− CT+ | AB+ CT+ |
|---|---|---|---|---|
| AB− CT− | — | 0.36 | 0.011 | 0.0034 |
| AB+ CT− | — | — | 0.0012 | 0.0001 |
| AB− CT+ | — | — | — | 0.0076 |
| AB+ CT+ | — | — | — | — |

The above experiment was repeated, with inclusion of an additional group treated with antibiotics prior to instillation of L. sakei (ATCC 15521) (FIG. 5), to demonstrate that goblet cell hyperplasia and mucin hypersecretion were induced specifically by C. tuberculostearicum. The conditions were designed to confirm that the characteristic pathogenic response did not simply represent a host response to instillation of any bacterial species into the sinus niche. L. sakei was selected because this species was present in high abundance in healthy mucosal samples, and was the most significantly depleted taxon in CRS patients. These results indicated that L. sakei is a protective sinus mucosal colonizer, and likely would not induce a pathogenic response.

Figure 7:
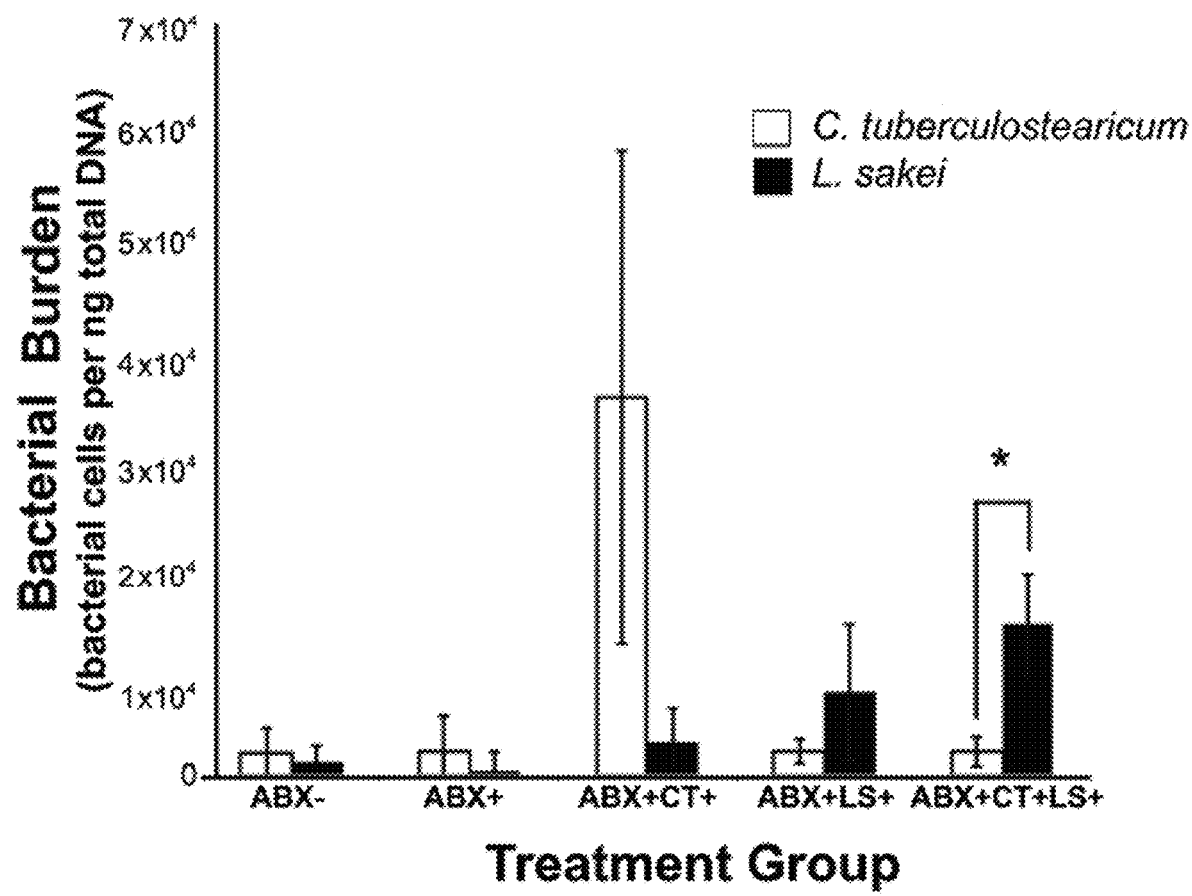
FIG. 7. Q-PCR quantification of *C. tuberculostearium* and *L. sakei* load in murine sinus tissue. Asterisk (*) denotes statistical significance ($p<0.05$). Total 16S rRNA copy number per species was normalized to known number of 16S rRNA copies per genome for each species.
Figure 8A:
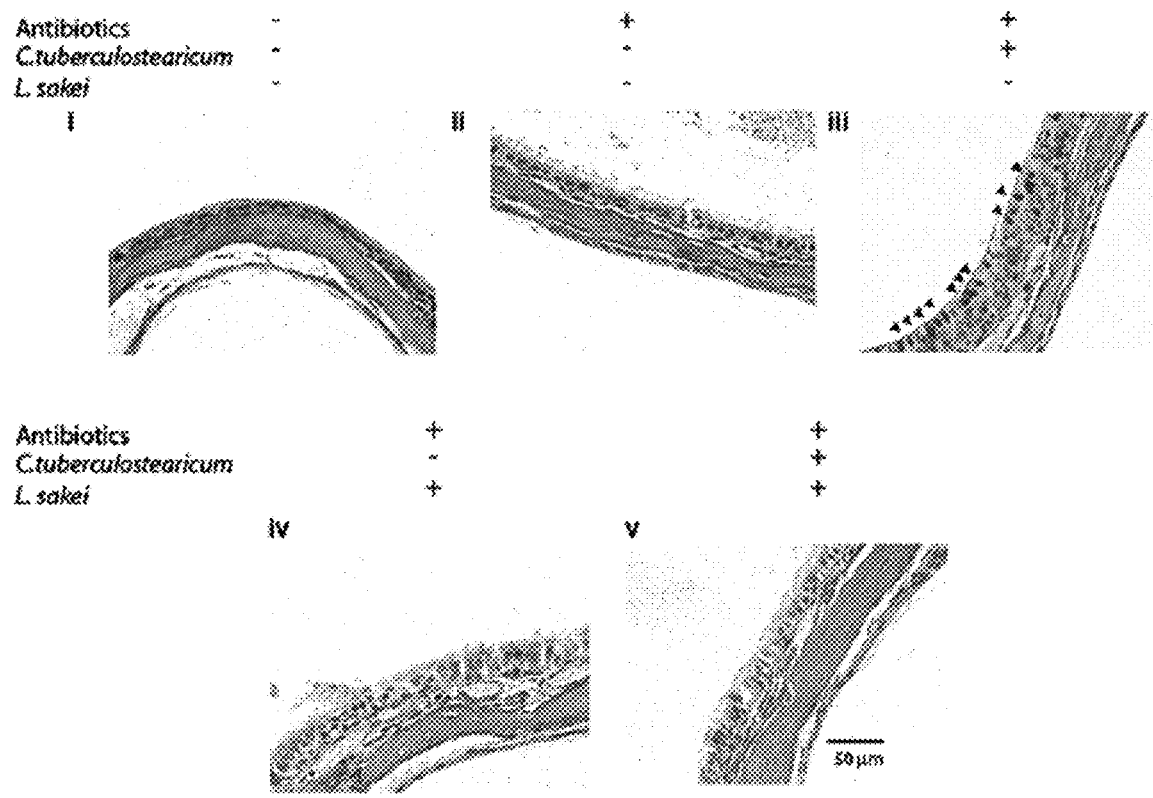
FIGS. 8A-8B.

Q-PCR was performed on all treatment groups to confirm that animals receiving bacterial inocula exhibited the presence of these species (FIG. 7). Histological imaging of the maxillary sinuses (FIG. 8A) demonstrated again that the antibiotic-treated and C. tuberculostearicum inoculated group exhibited significant increases in goblet cell hyperplasia and mucin hypersecretion (FIG. 8A, panel iii). Mice receiving identical numbers of L. sakei, however, demonstrated epithelial physiology comparable to that of control animals (no significant differences in goblet cell numbers; Table 3; FIG. 8A, panel iv). That L. sakei inoculated animals did not display the pathogenic response indicated that it was specifically due to C. tuberculostearium. Enumeration of goblet cell numbers in each treatment group confirmed these observations (FIG. 8B; Table 3).

Figure 8B:
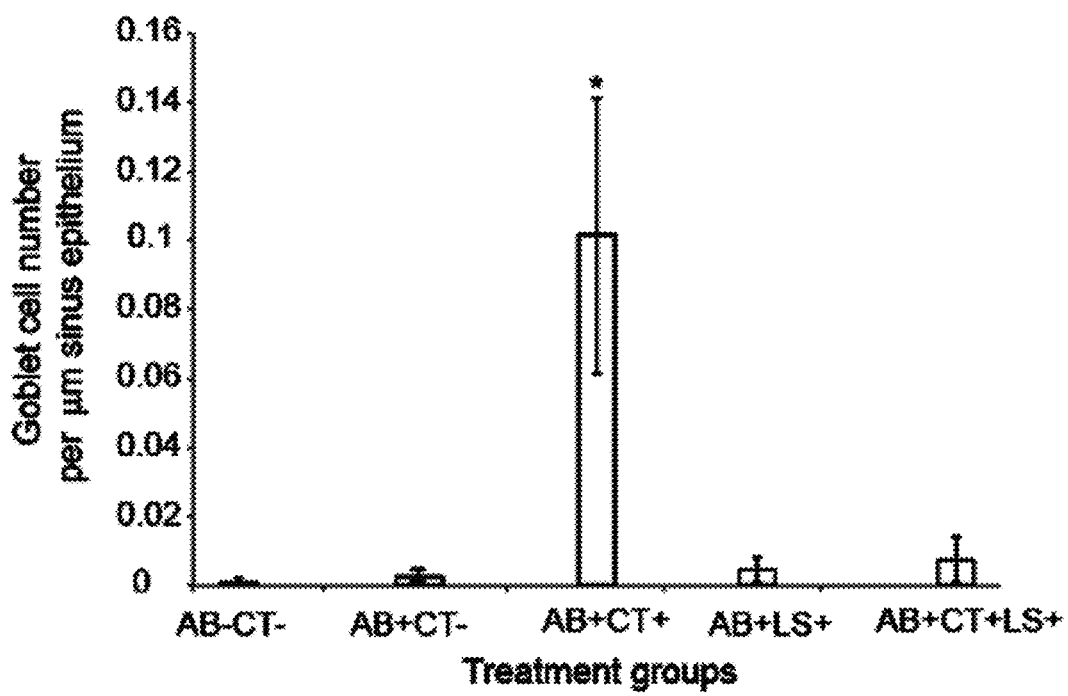

The collective data indicate that L. sakei is protective in the sinus mucosa. We next investigated whether co-instillation of L. sakei with C. tuberculostearicum could abrogate the goblet cell hyperplasia and mucin hypersecretion phenotype induced by C. tuberculostearicum, even in the context of a depleted native microbiota. Following treatment with antibiotics, equal numbers of both species were instilled into the sinuses of mice. Histological examination revealed sinus epithelia comparable to that of animals in the control groups (FIG. 8A, panel v), with no significant differences in goblet cell numbers observed across these groups (FIG. 8B and Table 3). Q-PCR analyses demonstrated significantly ($p<0.02$) reduced *C. tuberculostearicum* abundance in the co-instilled animals compared to animals infected with *C. tuberculostearicum* alone (FIG. 7). *L. sakei* numbers in these animals were, however, similar to those in animals treated with *L. sakei* alone (FIGS. 8A-8B). The data indicate that *L. sakei* protects the sinus epithelium, putatively through competitive inhibition of *C. tuberculostearicum. L. sakei* thus represents a novel, probiotic therapy for amelioration or prevention of sinus pathology, even in patients with severe sinus microbiome depletion.

TABLE 3

Significance values for comparative goblet cell number per μm of epithelial cell surface across mouse treatment groups (FIGS. 8A-8B).

| | AB− CT− | AB+ CT− | AB+ LS+ | AB+ CT+ | AB+ CT+ LS+ |
|---|---|---|---|---|---|
| AB− CT− | — | 1 | 0.2002 | 0.0099 | 0.2082 |
| AB+ CT− | — | — | 0.2002 | 0.0099 | 0.2082 |
| AB+ LS+ | — | — | — | 0.0118 | 0.5717 |
| AB+ CT+ | — | — | — | — | 0.0141 |
| AB+ CT+ LS+ | — | — | — | — | — |

TABLE X

Bacterial species negatively correlated with sinus symptom severity

| Phylum | Family | Taxon | prokMSA Name | Estimate | P value | Q value |
|---|---|---|---|---|---|---|
| Firmicutes | Lactobacillaceae | 3547 | *Lactobacillus frumenti* str. TMW 1.666 | −0.5324516 | 0.04998019 | 0.035270589 |
| Proteobacteria | Helicobacteraceae | 10520 | *Helicobacter* sp. blood isolate 964 | −0.5325229 | 0.04994373 | 0.035270589 |
| Proteobacteria | Campylobacteraceae | 10538 | *Arcobacter cryaerophilus* | −0.5332394 | 0.04957863 | 0.035270589 |
| Unclassified | Unclassified | 243 | hot spring clone OPB25 | −0.5332699 | 0.04956314 | 0.035270589 |
| Proteobacteria | Nitrospinaceae | 594 | uranium mining mill tailing clone GR-296.II.52 GR-296.I.52 | −0.5334925 | 0.04945017 | 0.035270589 |
| Firmicutes | Acholeplasmataceae | 3977 | Chinaberry yellows phytoplasma str. CbY1 | −0.53364 | 0.04937536 | 0.035270589 |
| Bacteroidetes | Porphyromonadaceae | 5429 | | −0.5336558 | 0.04936737 | 0.035270589 |
| Cyanobacteria | Chloroplasts | 5040 | *Solanum nigrum* | −0.5336963 | 0.04934686 | 0.035270589 |
| Proteobacteria | Bradyrhizobiaceae | 7390 | *Afipia geno*sp. 10 str. G8996 | −0.5336971 | 0.04934647 | 0.035270589 |
| Firmicutes | Lachnospiraceae | 2994 | termite gut clone Rs-L15 | −0.533732 | 0.04932878 | 0.035270589 |
| Synergistes | Unclassified | 117 | termite gut homogenate clone Rs-D89 | −0.5342366 | 0.04907378 | 0.035270589 |
| Bacteroidetes | Flavobacteriaceae | 5401 | *Capnocytophaga gingivalis* str. ChDC OS45 | −0.5343746 | 0.04900422 | 0.035270589 |
| Proteobacteria | Desulfobacteraceae | 10046 | *Desulfobacterium cetonicum* str. DSM 7267 oil recovery water | −0.5343791 | 0.04900192 | 0.035270589 |
| Verrucomicrobia | Verrucomicrobiaceae | 613 | hydrothermal vent polychaete mucous clone P. palm C 85 | −0.5344217 | 0.04898049 | 0.035270589 |
| Proteobacteria | Unclassified | 10427 | hydrothermal vent 9 degrees North East Rise Pacific Ocean clone CH3_17_BAC_16SrRNA_9N_EPR | −0.5344767 | 0.04895279 | 0.035270589 |
| Actinobacteria | Micrococcaceae | 1686 | *Yania halotolerans* str. YIM 70085 | −0.5345007 | 0.04894071 | 0.035270589 |
| Unclassified | Unclassified | 4410 | | −0.5345541 | 0.04891381 | 0.035270589 |
| Cyanobacteria | Unclassified | 5010 | LPP-group cyanobacterium isolate str. QSSC5cya QSSC5cya | −0.5346143 | 0.04888353 | 0.035270589 |
| Acidobacteria | Unclassified | 6357 | anaerobic benzene-degrading clone Cart-N4 | −0.5346545 | 0.04886331 | 0.035270589 |
| Proteobacteria | Unclassified | 8961 | *Calyptogena magnifica* symbiont | −0.5349561 | 0.04871181 | 0.035270589 |
| Firmicutes | Acholeplasmataceae | 3945 | Ash witches'-broom phytoplasma str. AshWB | −0.5352908 | 0.04854413 | 0.035270589 |
| Firmicutes | Lachnospiraceae | 2693 | ruminantium str. GA195 | −0.5353908 | 0.04849409 | 0.035270589 |
| Firmicutes | Peptococc/ Acidaminococc | 865 | *Selenomonas sputigena* str. ATCC 35185 | −0.5354898 | 0.04844462 | 0.035270589 |
| Firmicutes | Paenibacillaceae | 3641 | *Brevibacillus* sp. MN 47.2a | −0.5355341 | 0.04842245 | 0.035270589 |
| Planctomycetes | Planctomycetaceae | 4855 | aerobic basin clone CY0ARA026D10 | −0.5360602 | 0.0481602 | 0.035270589 |
| Firmicutes | Lactobacillaceae | 3696 | *Lactobacillus kalixensis* str. Kx127A2; LMG 22115T; DSM 16043T; CCUG 48459T | −0.536599 | 0.04789264 | 0.035270589 |
| Proteobacteria | Unclassified | 10259 | | −0.5369322 | 0.04772772 | 0.035270589 |
| Firmicutes | Unclassified | 2541 | UASB granular sludge clone UT-2 | −0.5369672 | 0.04771044 | 0.035270589 |
| Firmicutes | Lachnospiraceae | 2681 | termite gut homogenate clone Rs-K41 bacterium | −0.5370585 | 0.04766533 | 0.035270589 |

TABLE X-continued

Bacterial species negatively correlated with sinus symptom severity

| Phylum | Family | Taxon | prokMSA Name | Estimate | P value | Q value |
| --- | --- | --- | --- | --- | --- | --- |
| Proteobacteria | Bradyrhizobiaceae | 7126 | ground water deep-well injection disposal site radioactive wastes Tomsk-7 clone S15A-MN96 proteobacterium | −0.5371332 | 0.04762847 | 0.035270589 |
| Firmicutes | Syntrophomonadaceae | 2483 | trichloroethene-contaminated site clone FTLM142 bacterium | −0.5376491 | 0.04737434 | 0.035270589 |
| Firmicutes | Peptococc/Acidaminococc | 131 | pig feces clone | −0.5377144 | 0.04734226 | 0.035270589 |
| Proteobacteria | Unclassified | 8587 | Mars Odyssey Orbiter and encapsulation facility clone T5-3 | −0.5377735 | 0.04731322 | 0.035270589 |
| Bacteroidetes | Flavobacteriaceae | 5906 | *Capnocytophaga sputigena* str. ATCC 33612 | −0.5378696 | 0.04726602 | 0.035270589 |
| Bacteroidetes | Flavobacteriaceae | 5933 | *Flavobacterium columnare* str. PH-97028 (IAM 14821) | −0.5378938 | 0.04725415 | 0.035270589 |
| Firmicutes | Lachnospiraceae | 2965 | oral endodontic infection clone MCE9_173 | −0.5381045 | 0.04715086 | 0.035270589 |
| Actinobacteria | Micrococcaceae | 1494 | *Arthrobacter agilis* str. DSM 20550 | −0.5383154 | 0.04704757 | 0.035270589 |
| BRC1 | Unclassified | 5143 | soil clone PBS-II-1 | −0.5383959 | 0.04700824 | 0.035270589 |
| Firmicutes | Enterococcaceae | 3298 | *Enterococcus saccharolyticus* str. LMG 11427 | −0.5391099 | 0.04666012 | 0.035270589 |
| Cyanobacteria | Unclassified | 5038 | Rumen isolate str. YS2 | −0.5392866 | 0.04657427 | 0.035270589 |
| Firmicutes | Lachnospiraceae | 4335 | termite gut homogenate clone Rs-N86 bacterium | −0.5392971 | 0.04656915 | 0.035270589 |
| Firmicutes | Aerococcaceae | 3504 | *Marinilactibacillus psychrotolerans* str. O21 | −0.5397087 | 0.04636966 | 0.035270589 |
| Bacteroidetes | Unclassified | 5257 | marine? clone KD3-67 | −0.5398265 | 0.04631263 | 0.035270589 |
| Firmicutes | Peptococc/Acidaminococc | 534 | chlorobenzene-degrading consortium clone IIA-26 | −0.5401839 | 0.04614008 | 0.035270589 |
| Spirochaetes | Spirochaetaceae | 6526 | *Treponema* sp. str. 7CPL208 | −0.5402284 | 0.0461186 | 0.035270589 |
| Actinobacteria | Micrococcaceae | 1573 | *Arthrobacter nicotianae* str. SB42 | −0.5405694 | 0.04595441 | 0.035270589 |
| Proteobacteria | Desulfoarculaceae | 10227 | marine sediment clone Bol11 | −0.5409671 | 0.04576348 | 0.035270589 |
| Firmicutes | Clostridiaceae | 4278 | granular sludge clone R1p16 | −0.5409777 | 0.04575841 | 0.035270589 |
| Proteobacteria | Unclassified | 7060 | | −0.5410353 | 0.0457308 | 0.035270589 |
| Bacteroidetes | Unclassified | 5785 | Mono Lake at depth 35 m station 6 Jul. 2000 clone ML635J-56 | −0.5413643 | 0.04557336 | 0.035270589 |
| Firmicutes | Streptococcaceae | 3499 | *Streptococcus constellatus* str. ATCC27823 | −0.5416222 | 0.04545022 | 0.035270589 |
| Firmicutes | Clostridiaceae | 4177 | *Clostridium subterminale* DSM 2636 | −0.5419209 | 0.04530792 | 0.035270589 |
| Bacteroidetes | Rikenellaceae | 5889 | termite gut homogenate clone Rs-F73 bacterium | −0.5420021 | 0.0452693 | 0.035270589 |
| Proteobacteria | Bdellovibrionaceae | 10010 | uranium mining waste pile clone JG37-AG-139 proteobacterium | −0.5422324 | 0.04515985 | 0.035270589 |
| Firmicutes | Peptococc/Acidaminococc | 392 | oral endodontic infection clone MCE7_134 | −0.5424949 | 0.04503537 | 0.035270589 |
| Bacteroidetes | Sphingobacteriaceae | 5513 | crevicular epithelial cells clone AZ123 | −0.5425299 | 0.04501877 | 0.035270589 |
| Firmicutes | Mycoplasmataceae | 3929 | *Mycoplasma gypsbengalensis* str. Gb-V33 | −0.5427064 | 0.04493525 | 0.035270589 |
| Firmicutes | Clostridiaceae | 4300 | termite gut clone Rs-060 | −0.5428522 | 0.04486631 | 0.035270589 |
| Proteobacteria | Campylobacteraceae | 10484 | *Campylobacter helveticus* | −0.5430959 | 0.04475126 | 0.035270589 |
| OP10 | Unclassified | 514 | sludge clone SBRA136 | −0.5432395 | 0.04468356 | 0.035270589 |
| Proteobacteria | Syntrophobacteraceae | 10221 | granular sludge clone R3p4 | −0.5433823 | 0.04461634 | 0.035270589 |
| Firmicutes | Lactobacillaceae | 3330 | *Lactobacillus kitasatonis* str. KM9212 | −0.5437728 | 0.04443286 | 0.035270589 |
| BRC1 | Unclassified | 118 | penguin droppings sediments clone KD1-1 | −0.5440147 | 0.04431948 | 0.035270589 |
| Firmicutes | Peptococc/Acidaminococc | 39 | forested wetland clone RCP2-71 | −0.5441698 | 0.04424689 | 0.035270589 |
| Proteobacteria | Pasteurellaceae | 9213 | *Haemophilus quentini* str. MCCM 02026 | −0.544316 | 0.04417854 | 0.035270589 |
| Firmicutes | Streptococcaceae | 3629 | *Streptococcus mutans* str. UA96 | −0.5443712 | 0.04415277 | 0.035270589 |
| Proteobacteria | Unclassified | 9760 | deep marine sediment clone MB-A2-137 | −0.5450115 | 0.0438545 | 0.035270589 |

TABLE X-continued

Bacterial species negatively correlated with sinus symptom severity

| Phylum | Family | Taxon | prokMSA Name | Estimate | P value | Q value |
|---|---|---|---|---|---|---|
| Firmicutes | Unclassified | 926 | | −0.5457011 | 0.04353492 | 0.035270589 |
| Firmicutes | Staphylococcaceae | 3524 | *Gemella haemolysans* | −0.5458225 | 0.04347884 | 0.035270589 |
| Proteobacteria | Syntrophobacteraceae | 10021 | uranium mill tailings soil sample clone Sh765B-TzT-29 proteobacterium | −0.546055 | 0.04337153 | 0.035270589 |
| Actinobacteria | Micrococcaceae | 1593 | *Arthrobacter globiformis* | −0.5462532 | 0.04328029 | 0.035270589 |
| Proteobacteria | Desulfobacteraceae | 9875 | hydrothermal sediment clone AF420354 | −0.5463408 | 0.04323997 | 0.035270589 |
| Cyanobacteria | Chloroplasts | 4966 | *Adiantum pedatum* | −0.5470294 | 0.04292415 | 0.035270589 |
| Bacteroidetes | Prevotellaceae | 5893 | tongue dorsa clone DO045 | −0.5471467 | 0.04287049 | 0.035270589 |
| Firmicutes | Peptococc/Acidaminococc | 562 | oral endodontic infection clone MCE10_265 | −0.5472263 | 0.04283412 | 0.035270589 |
| Chlorobi | Unclassified | 636 | benzene-degrading nitrate-reducing consortium clone Cart-N3 bacterium | −0.5473972 | 0.04275611 | 0.035270589 |
| Firmicutes | Carnobacteriaceae | 3536 | | −0.5475614 | 0.04268128 | 0.035270589 |
| Bacteroidetes | Flavobacteriaceae | 5473 | | −0.5478064 | 0.04256979 | 0.035270589 |
| Proteobacteria | Syntrophobacteraceae | 9845 | uranium mining waste pile clone JG37-AG-128 proteobacterium | −0.5484553 | 0.0422755 | 0.035270589 |
| Proteobacteria | Campylobacteraceae | 10540 | *Campylobacter showae* str. LMG 12636 | −0.5489328 | 0.0420599 | 0.035270589 |
| Proteobacteria | Sphingomonadaceae | 7100 | *Novosphingobium capsulatum* str. GIFU11526 | −0.5490852 | 0.04199126 | 0.035270589 |
| Proteobacteria | Bradyrhizobiaceae | 6887 | *Bradyrhizobium* str. YB2 | −0.5492974 | 0.04189579 | 0.035270589 |
| Chloroflexi | Unclassified | 76 | DCP-dechlorinating consortium clone SHA-147 | −0.5500398 | 0.04156317 | 0.035270589 |
| Firmicutes | Clostridiaceae | 4265 | termite gut homogenate clone Rs-N70 bacterium | −0.5500563 | 0.04155579 | 0.035270589 |
| Bacteroidetes | Flavobacteriaceae | 5436 | Arctic sea ice ARK10004 | −0.5501646 | 0.04150741 | 0.035270589 |
| Actinobacteria | Unclassified | 1898 | termite gut homogenate clone Rs-J10 bacterium | −0.5503548 | 0.0414226 | 0.035270589 |
| Firmicutes | Aerococcaceae | 3631 | *Abiotrophia defectiva* str. GIFU12707 (ATCC49176) | −0.5504543 | 0.04137826 | 0.035270589 |
| Firmicutes | Streptococcaceae | 3753 | *Streptococcus suis* str. 8074 | −0.5505636 | 0.04132961 | 0.035270589 |
| Bacteroidetes | Flexibacteraceae | 6124 | *Flexibacter flexilis* subsp. *pelliculosus* str. IFO 16028 subsp. | −0.5507177 | 0.04126111 | 0.035270589 |
| Firmicutes | Enterococcaceae | 3382 | | −0.5508457 | 0.04120423 | 0.035270589 |
| Firmicutes | Leuconostocaceae | 3573 | *Leuconostoc ficulneum* str. FS-1 | −0.5511595 | 0.0410651 | 0.035270589 |
| Firmicutes | Streptococcaceae | 3422 | *Streptococcus thermophilus* str. DSM 20617 | −0.5511839 | 0.04105433 | 0.035270589 |
| Firmicutes | Lachnospiraceae | 4315 | termite gut homogenate clone Rs-N94 bacterium | −0.5512027 | 0.04104598 | 0.035270589 |
| Unclassified | Unclassified | 7444 | | −0.5513268 | 0.04099107 | 0.035270589 |
| Bacteroidetes | Flexibacteraceae | 6261 | Arctic sea ice cryoconite clone ARKCRY-50 | −0.5515557 | 0.04088996 | 0.035270589 |
| Planctomycetes | Planctomycetaceae | 4948 | anoxic basin clone CY0ARA027D01 | −0.5524994 | 0.0404749 | 0.035270589 |
| Firmicutes | Streptococcaceae | 3253 | derived cheese sample clone 32CR | −0.5527952 | 0.04034546 | 0.035270589 |
| Firmicutes | Clostridiaceae | 4614 | *Clostridium* sp. str. JC3 | −0.5534251 | 0.04007081 | 0.035270589 |
| Bacteroidetes | Flavobacteriaceae | 5267 | bacterioplankton clone AEGEAN_179 | −0.5535169 | 0.04003091 | 0.035270589 |
| Natronoanaerobium | Unclassified | 4377 | Mono Lake at depth 35 m station 6 Jul. 2000 clone ML635J-65 G + C | −0.5538773 | 0.03987448 | 0.035270589 |
| OP9/JS1 | Unclassified | 2489 | Guaymas Basin hydrothermal vent sediments clone B01R005 | −0.5543007 | 0.0396913 | 0.035270589 |
| Chloroflexi | Unclassified | 2534 | forest soil clone S085 | −0.5543422 | 0.03967338 | 0.035270589 |
| Bacteroidetes | Unclassified | 5957 | hydrothermal vent polychaete mucous clone P. palm C/A 20 | −0.5543543 | 0.03966819 | 0.035270589 |
| Firmicutes | Lactobacillaceae | 3521 | *Pediococcus inopinatus* str. DSM 20285 | −0.555167 | 0.03931844 | 0.035270589 |
| Firmicutes | Unclassified | 77 | thermal soil clone YNPFFP9 | −0.5552835 | 0.03926852 | 0.035270589 |
| Firmicutes | Clostridiaceae | 4550 | swine intestine clone p-320-a3 | −0.5558022 | 0.0390467 | 0.035270589 |
| Firmicutes | Lachnospiraceae | 2668 | termite gut homogenate clone Rs-G40 bacterium | −0.5558071 | 0.03904461 | 0.035270589 |
| Actinobacteria | Micrococcaceae | 1557 | *Arthrobacter oxydans* str. DSM 20119 | −0.5560342 | 0.03894779 | 0.035270589 |

TABLE X-continued

Bacterial species negatively correlated with sinus symptom severity

| Phylum | Family | Taxon | prokMSA Name | Estimate | P value | Q value |
| --- | --- | --- | --- | --- | --- | --- |
| Firmicutes | Clostridiaceae | 4459 | termite gut clone Rs-109 | −0.5567823 | 0.03863011 | 0.035270589 |
| Bacteroidetes | Flavobacteriaceae | 5521 | Flavobacteriaceae str. SW269 | −0.5568853 | 0.03858655 | 0.035270589 |
| Proteobacteria | Campylobacteraceae | 10397 | groundwater clone 1006 | −0.5570026 | 0.03853694 | 0.035270589 |
| Proteobacteria | Unclassified | 9876 | deep marine sediment clone MB-B2-106 | −0.5570065 | 0.03853531 | 0.035270589 |
| Firmicutes | Lachnospiraceae | 4514 | termite gut homogenate clone Rs-B34 bacterium | −0.5570651 | 0.03851051 | 0.035270589 |
| Proteobacteria | Polyangiaceae | 9733 | bacterioplankton clone ZA3735c | −0.5574153 | 0.03836281 | 0.035270589 |
| Firmicutes | Unclassified | 522 | UASB granular sludge clone UT-1 | −0.5575107 | 0.03832264 | 0.035270589 |
| Firmicutes | Streptococcaceae | 3722 | *Lactococcus* Il1403 subsp. *lactis* str. IL1403 | −0.5578807 | 0.03816718 | 0.035270589 |
| Firmicutes | Peptococc/ Acidaminococc | 304 | *Selenomonas ruminantium* str.JCM6582 | −0.5580707 | 0.0380875 | 0.035270589 |
| Firmicutes | Lactobacillaceae | 3885 | *Pediococcus pentosaceus* | −0.5582024 | 0.03803234 | 0.035270589 |
| Proteobacteria | Sphingomonadaceae | 7440 | *Sphingobium chungbukense* str. DJ77 | −0.558408 | 0.03794637 | 0.035270589 |
| Firmicutes | Aerococcaceae | 3326 | *Nostocoida limicola* I str. Ben206 | −0.558438 | 0.03793384 | 0.035270589 |
| Bacteroidetes | Flexibacteraceae | 5602 | | −0.558608 | 0.03786285 | 0.035270589 |
| Proteobacteria | Polyangiaceae | 10298 | marine tidal mat clone BTM36 | −0.5588222 | 0.03777357 | 0.035270589 |
| Firmicutes | Bacillaceae | 3900 | *Bacillus licheniformis* str. DSM 13 | −0.5588343 | 0.03776853 | 0.035270589 |
| Bacteroidetes | Rikenellaceae | 5892 | anoxic bulk soil flooded rice microcosm clone BSV73 | −0.559133 | 0.03764434 | 0.035270589 |
| Proteobacteria | Pasteurellaceae | 8195 | *Haemophilus influenzae* str. R2866 | −0.5591662 | 0.03763053 | 0.035270589 |
| Chlorobi | Chlorobiaceae | 859 | *Chlorobium phaeovibrioides* str. 2631 | −0.5598611 | 0.03734276 | 0.035270589 |
| Firmicutes | Clostridiaceae | 4477 | termite gut homogenate clone Rs-N85 bacterium | −0.5599449 | 0.03730819 | 0.035270589 |
| Proteobacteria | Unclassified | 244 | deep marine sediment clone MB-C2-152 | −0.5600791 | 0.03725282 | 0.035270589 |
| Bacteroidetes | Flavobacteriaceae | 6248 | *Capnocytophaga* sp. oral strain str. S3 | −0.56046 | 0.03709607 | 0.035270589 |
| Proteobacteria | Unclassified | 10084 | acid mine drainage clone AS6 | −0.5606514 | 0.03701749 | 0.035270589 |
| Firmicutes | Streptococcaceae | 3588 | *Streptococcus downei* str. ATCC 33748 | −0.5606556 | 0.03701576 | 0.035270589 |
| Firmicutes | Peptococc/ Acidaminococc | 1036 | Great Artesian Basin clone G07 | −0.560657 | 0.0370152 | 0.035270589 |
| Chloroflexi | Unclassified | 2397 | deep marine sediment clone MB-C2-I27 | −0.561111 | 0.0368293 | 0.035270589 |
| Actinobacteria | Micrococcaceae | 2020 | *Rothia dentocariosa* str. ChDC B200 | −0.5612027 | 0.03679183 | 0.035270589 |
| Bacteroidetes | Unclassified | 5353 | trichloroethene-contaminated site clone FTLpost3 bacterium | −0.561455 | 0.03668889 | 0.035270589 |
| Bacteroidetes | Flavobacteriaceae | 5991 | *Tenacibaculum ovolyticum* str. IAM14318 | −0.5617321 | 0.03657605 | 0.035270589 |
| Proteobacteria | Sphingomonadaceae | 7036 | *Lutibacterium anuloederans* str. LC8 | −0.562055 | 0.03644492 | 0.035270589 |
| Cyanobacteria | Chloroplasts | 5147 | *Emiliania huxleyi* str. Plymouth Marine Laborator PML 92 | −0.5620697 | 0.03643899 | 0.035270589 |
| Actinobacteria | Acidimicrobiaceae | 1090 | | −0.5623333 | 0.03633219 | 0.035270589 |
| Proteobacteria | Unclassified | 9813 | hydrothermal sediment clone AF420340 | −0.5624152 | 0.03629906 | 0.035270589 |
| Firmicutes | Enterococcaceae | 3433 | *Tetragenococcus muriaticus* | −0.5626691 | 0.03619651 | 0.035270589 |
| Firmicutes | Acholeplasmataceae | 4044 | | −0.5626807 | 0.03619181 | 0.035270589 |
| TM7 | Unclassified | 8040 | oral cavity clone BE109 | −0.5630985 | 0.03602354 | 0.035270589 |
| Bacteroidetes | Porphyromonadaceae | 5295 | swine intestine clone p-987-s962-5 | −0.563282 | 0.03594978 | 0.035270589 |
| Bacteroidetes | Flavobacteriaceae | 5914 | *Psychroserpens burtonensis* str. S2-64 | −0.563714 | 0.03577667 | 0.035270589 |
| Firmicutes | Lachnospiraceae | 4613 | rumen clone 3C0d-3 | −0.5638647 | 0.03571638 | 0.035270589 |
| Firmicutes | Acholeplasmataceae | 4046 | Pigeon pea witches'-broom mycoplasma-like organism | −0.56396 | 0.03567834 | 0.035270589 |
| Bacteroidetes | Flavobacteriaceae | 6269 | acidic forest soil clone UC1 | −0.5640842 | 0.03562876 | 0.035270589 |
| OP9/JS1 | Unclassified | 969 | DCP-dechlorinating consortium clone SHA-1 | −0.5641236 | 0.03561305 | 0.035270589 |
| Firmicutes | Clostridiaceae | 4180 | termite gut homogenate clone Rs-M23 bacterium | −0.5642019 | 0.03558187 | 0.035270589 |

TABLE X-continued

Bacterial species negatively correlated with sinus symptom severity

| Phylum | Family | Taxon | prokMSA Name | Estimate | P value | Q value |
|---|---|---|---|---|---|---|
| Cyanobacteria | Chloroplasts | 4976 | *Calypogeia muelleriana* | −0.5642267 | 0.03557199 | 0.035270589 |
| Firmicutes | Enterococcaceae | 3261 | *Enterococcus mundtii* str. LMG 10748 | −0.5647034 | 0.03538246 | 0.035270589 |
| Actinobacteria | Micrococcaceae | 1324 | glacial ice isolate str. CanDirty1 | −0.5655964 | 0.03502939 | 0.035270589 |
| Firmicutes | Peptococc/Acidaminococc | 761 | *Anaeroglobus geminatus* str. AIP313.00; CIP 106856; CCUG 44773 | −0.5657127 | 0.0349836 | 0.035270589 |
| Bacteroidetes | Unclassified | 5475 | SHA-25 clone | −0.5660295 | 0.03485913 | 0.035270589 |
| Planctomycetes | Planctomycetaceae | 4831 | *Planctomyces brasiliensis* | −0.566052 | 0.0348503 | 0.035270589 |
| Firmicutes | Lachnospiraceae | 4510 | termite gut homogenate clone Rs-Q53 bacterium | −0.5663472 | 0.0347346 | 0.035270589 |
| Firmicutes | Lactobacillaceae | 3767 | *Lactobacillus suebicus* str. CECT 5917T | −0.5665992 | 0.03463607 | 0.035270589 |
| Firmicutes | Peptococc/Acidaminococc | 709 | *Selenomonas ruminantium* str. S20 | −0.5670817 | 0.03444798 | 0.035270589 |
| Proteobacteria | Unclassified | 9884 | forested wetland clone RCP2-62 | −0.5671464 | 0.03442282 | 0.035270589 |
| Firmicutes | Leuconostocaceae | 3497 | Weissella koreensis S-5673 | −0.5673939 | 0.03432668 | 0.035270589 |
| Firmicutes | Enterococcaceae | 3713 | *Enterococcus cecorum* str. ATCC43198 | −0.5677953 | 0.03417121 | 0.035270589 |
| Firmicutes | Lactobacillaceae | 3566 | *Lactobacillus pontis* str. LTH 2587 | −0.5690756 | 0.03367873 | 0.035270589 |
| Firmicutes | Unclassified | 4536 | Mono Lake at depth 35 m station 6 Jul. 2000 clone ML635J-14 G + C | −0.5692171 | 0.03362463 | 0.035270589 |
| Firmicutes | Unclassified | 3481 | | −0.5692343 | 0.03361806 | 0.035270589 |
| Proteobacteria | Syntrophobacteraceae | 9661 | DCP-dechlorinating consortium clone SHD-1 | −0.5696648 | 0.0334539 | 0.035270589 |
| Proteobacteria | Desulfobacteraceae | 10364 | marine surface sediment clone SB2 | −0.5697152 | 0.03343469 | 0.035270589 |
| Firmicutes | Lachnospiraceae | 2943 | human thigh wound isolate str. MDA2477 | −0.5708144 | 0.03301837 | 0.035270589 |
| Firmicutes | Enterococcaceae | 3318 | *Enterococcus ratti* str. ATCC 700914 | −0.5711715 | 0.03288393 | 0.035270589 |
| Bacteroidetes | Porphyromonadaceae | 6012 | mouse feces clone L11-6 | −0.5712018 | 0.03287255 | 0.035270589 |
| Firmicutes | Clostridiaceae | 4554 | termite gut clone Rs-068 | −0.571372 | 0.03280865 | 0.035270589 |
| Firmicutes | Lactobacillaceae | 3490 | *Lactobacillus suntoryeus* str. LH | −0.5714735 | 0.03277059 | 0.035270589 |
| Firmicutes | Clostridiaceae | 4582 | swine intestine clone p-2600-9F5 | −0.5725013 | 0.03238692 | 0.035270589 |
| Firmicutes | Peptococc/Acidaminococc | 242 | *Desulfosporosinus orientis* str. DSMZ 7493 | −0.5726663 | 0.03232564 | 0.035270589 |
| Firmicutes | Streptococcaceae | 3907 | aortic heart valve patient with endocarditis clone v6 | −0.5727726 | 0.03228622 | 0.035270589 |
| Firmicutes | Peptococc/Acidaminococc | 710 | *Centipeda periodontii* str. HB-2 | −0.5729265 | 0.03222922 | 0.035270589 |
| Cyanobacteria | Chloroplasts | 5183 | *Pisum sativum*-chloroplast | −0.5756529 | 0.03123133 | 0.035270589 |
| Cyanobacteria | Chloroplasts | 5192 | *Cycas revoluta* | −0.5759699 | 0.03111681 | 0.035270589 |
| Firmicutes | Lachnospiraceae | 2991 | rumen clone 3C3d-8 | −0.5761139 | 0.03106487 | 0.035270589 |
| Firmicutes | Enterococcaceae | 3881 | *Enterococcus dispar* str. LMG 13521 | −0.5764427 | 0.03094657 | 0.035270589 |
| Bacteroidetes | Flavobacteriaceae | 5836 | *Capnocytophaga granulosa* str. LMG 12119; FDC SD4 | −0.5766249 | 0.03088116 | 0.035270589 |
| Firmicutes | Peptococc/Acidaminococc | 300 | benzene-contaminated groundwater clone ZZ12C8 | −0.5787987 | 0.03010865 | 0.035270589 |
| Bacteroidetes | Unclassified | 5784 | fruiting body Pleurotus eryngii clone PE01 | −0.5792647 | 0.02994496 | 0.035270589 |
| Firmicutes | Bacillaceae | 3848 | *Bacillus* sp. str. TUT1007 | −0.5793954 | 0.02989915 | 0.035270589 |
| Firmicutes | Carnobacteriaceae | 3792 | *Carnobacterium* sp. str. D35 | −0.5804968 | 0.02951531 | 0.035270589 |
| Firmicutes | Lachnospiraceae | 4533 | termite gut homogenate clone Rs-N06 bacterium | −0.581153 | 0.02928835 | 0.035270589 |
| Unclassified | Unclassified | 651 | | −0.5811737 | 0.02928121 | 0.035270589 |
| Bacteroidetes | Flavobacteriaceae | 6246 | crevicular epithelial cells clone BU084 | −0.5814157 | 0.02919784 | 0.035270589 |
| Firmicutes | Lachnospiraceae | 4434 | termite gut homogenate clone Rs-K11 bacterium | −0.5814826 | 0.02917485 | 0.035270589 |
| Firmicutes | Lactobacillaceae | 3418 | *Lactobacillus* subsp. *aviarius* | −0.5814892 | 0.02917259 | 0.035270589 |
| Firmicutes | Clostridiaceae | 4297 | | −0.5818952 | 0.02903323 | 0.035270589 |
| Proteobacteria | Polyangiaceae | 9671 | hydrothermal sediment clone AF420357 | −0.5821323 | 0.02895206 | 0.035270589 |
| Firmicutes | Acholeplasmataceae | 3976 | | −0.5828049 | 0.0287228 | 0.035270589 |
| Firmicutes | Acholeplasmataceae | 3961 | Clover yellow edge mycoplasma-like organism | −0.5834912 | 0.02849025 | 0.035270589 |

TABLE X-continued

Bacterial species negatively correlated with sinus symptom severity

| Phylum | Family | Taxon | prokMSA Name | Estimate | P value | Q value |
|---|---|---|---|---|---|---|
| Bacteroidetes | Flavobacteriaceae | 5301 | | −0.5838861 | 0.02835706 | 0.035270589 |
| Firmicutes | Streptococcaceae | 3685 | *Streptococcus gordonii* str. ATCC 10558 | −0.5840426 | 0.02830442 | 0.035270589 |
| Actinobacteria | Micrococcaceae | 2063 | *Rothia dentocariosa* str. ATCC 17931 | −0.5849591 | 0.02799754 | 0.035270589 |
| Firmicutes | Clostridiaceae | 4272 | termite gut homogenate clone Rs-M34 bacterium | −0.5856846 | 0.02775641 | 0.035270589 |
| Synergistes | Unclassified | 353 | UASB reactor granular sludge clone PD-UASB-13 G + C | −0.5862744 | 0.02756153 | 0.035270589 |
| Fusobacteria | Fusobacteriaceae | 721 | human mouth clone P2PB_51 | −0.5863706 | 0.02752982 | 0.035270589 |
| Firmicutes | Clostridiaceae | 4524 | termite gut clone Rs-093 | −0.5872218 | 0.0272506 | 0.035270589 |
| Firmicutes | Acholeplasmataceae | 4045 | Chinaberry yellows phytoplasma | −0.5874789 | 0.0271667 | 0.035270589 |
| Firmicutes | Lachnospiraceae | 4155 | termite gut homogenate clone Rs-K92 bacterium | −0.5883278 | 0.02689095 | 0.035270589 |
| Firmicutes | Lactobacillaceae | 3703 | *Lactobacillus salivarius* str. RA2115 | −0.5896055 | 0.02647992 | 0.035270589 |
| Firmicutes | Clostridiaceae | 4622 | termite gut clone Rs-L36 | −0.590871 | 0.02607745 | 0.035270589 |
| Firmicutes | Aerococcaceae | 3833 | Carnobacterium alterfunditum | −0.5911531 | 0.02598836 | 0.035270589 |
| Firmicutes | Lachnospiraceae | 4540 | termite gut homogenate clone Rs-M18 bacterium | −0.5918608 | 0.02576588 | 0.035270589 |
| Firmicutes | Streptococcaceae | 3251 | *Streptococcus cristatus* str. ATCC 51100 | −0.5919206 | 0.02574714 | 0.035270589 |
| TM7 | Unclassified | 2697 | midgut homogenate *Pachnoda ephippiata* larva clone PeM47 | −0.591935 | 0.02574265 | 0.035270589 |
| Chloroflexi | Unclassified | 258 | DCP-dechlorinating consortium clone SHD-14 | −0.5925901 | 0.02553809 | 0.035270589 |
| Firmicutes | Aerococcaceae | 3840 | *Trichococcus pasteurii* str. KoTa2 | −0.5926609 | 0.02551607 | 0.035270589 |
| Proteobacteria | Neisseriaceae | 8143 | subgingival dental plaque clone AK105 | −0.5935762 | 0.02523253 | 0.035270589 |
| Firmicutes | Acholeplasmataceae | 3975 | Black raspberry witches'-broom phytoplasma str. BRWB witches'-broom | −0.5940016 | 0.02510154 | 0.035270589 |
| Firmicutes | Streptococcaceae | 3543 | | −0.5975365 | 0.02403278 | 0.035270589 |
| Chloroflexi | Unclassified | 2339 | uranium mill tailings soil sample clone Sh765B-TzT-20 bacterium | −0.6019879 | 0.02273596 | 0.035270589 |
| Firmicutes | Unclassified | 3289 | *Isobaculum melis* CCUG 37660T | −0.6020217 | 0.02272631 | 0.035270589 |
| Firmicutes | Clostridiaceae | 4475 | termite gut homogenate clone Rs-N02 bacterium | −0.6038353 | 0.02221351 | 0.035270589 |
| Firmicutes | Enterococcaceae | 3598 | *Enterococcus solitarius* str. DSM 5634 | −0.6071271 | 0.02130506 | 0.035270589 |
| Firmicutes | Clostridiaceae | 4310 | termite gut clone Rs-056 | −0.6072521 | 0.02127112 | 0.035270589 |
| Firmicutes | Enterococcaceae | 3680 | *Melissococcus plutonius* str. NCDO 2440 | −0.609524 | 0.02066141 | 0.035270589 |
| Firmicutes | Peptococc/ Acidaminococc | 150 | | −0.6166294 | 0.01883948 | 0.035270589 |
| Chlorobi | Unclassified | 549 | benzene-degrading nitrate-reducing consortium clone Cart-N2 bacterium | −0.6183396 | 0.01841973 | 0.035270589 |
| Firmicutes | Lactobacillaceae | 3526 | *Lactobacillus sakei* | −0.6198186 | 0.01806246 | 0.035270589 |
| Firmicutes | Lachnospiraceae | 4281 | granular sludge clone UASB_brew_B86 | −0.6271224 | 0.01637464 | 0.035270589 |
| Bacteroidetes | Flavobacteriaceae | 5726 | *Bergeyella* sp. oral AK152 clone | −0.6281038 | 0.01615736 | 0.035270589 |
| Firmicutes | Lachnospiraceae | 4512 | granular sludge clone UASB_brew_B25 | −0.6320073 | 0.01531468 | 0.035270589 |
| Firmicutes | Lachnospiraceae | 4331 | granular sludge clone UASB_brew_B84 | −0.6379284 | 0.01410088 | 0.035270589 |
| Firmicutes | Lactobacillaceae | 3547 | *Lactobacillus frumenti* str. TMW 1.666 | −0.5324516 | 0.04998019 | 0.035270589 |

1. N. F. Ray et al., Healthcare expenditures for sinusitis in 1996: contributions of asthma, rhinitis, and other airway disorders. *The Journal of allergy and clinical immunology* 103, 408 (March, 1999).
2. D. V. Wallace et al., The diagnosis and management of rhinitis: an updated practice parameter. *J Allergy Clin Immunol* 122, S1 (August, 2008).
3. M. F. Stephenson et al., Molecular characterization of the polymicrobial flora in chronic rhinosinusitis. *J Otolaryngol Head Neck Surg* 39, 182 (April).
4. P. W. Doyle, J. D. Woodham, Evaluation of the microbiology of chronic ethmoid sinusitis. *J Clin Microbiol* 29, 2396 (November, 1991).
5. M. A. Biel et al., Evaluation of the microbiology of chronic maxillary sinusitis. *Ann Otol Rhinol Laryngol* 107, 942 (November, 1998).
6. I. Brook, E. H. Frazier, M. E. Gher, Jr., Microbiology of periapical abscesses and associated maxillary sinusitis. *J Periodontol* 67, 608 (June, 1996).
7. R. S. Jiang, J. F. Lin, C. Y. Hsu, Correlation between bacteriology of the middle meatus and ethmoid sinus in chronic sinusitis. *J Laryngol Otol* 116, 443 (June, 2002).
8. K. P. Lemon et al., Comparative analyses of the bacterial microbiota of the human nostril and oropharynx. *MBiol*, (2010).
9. T. D. Lawley et al., Antibiotic treatment of *Clostridium difficile* carrier mice triggers a supershedder state, spore-mediated transmission, and severe disease in immunocompromised hosts. *Infect Immun* 77, 3661 (September, 2009).
10. Y. Dong, F. Manfredini, G. Dimopoulos, Implication of the mosquito midgut microbiota in the defense against malaria parasites. *PLoS Pathog* 5, e1000423 (May, 2009).
11. E. K. Costello et al., Bacterial community variation in human body habitats across space and time. *Science* 326, 1694 (Dec. 18, 2009).
12. D. H. Kim et al., Up-regulation of MUC5AC and MUC5B mucin genes in chronic rhinosinusitis. *Arch Otolaryngol Head Neck Surg* 130, 747 (June, 2004).
13. J. N. Baraniuk et al., Neuropathology in rhinosinusitis. *Am J Respir Crit Care Med* 171, 5 (Jan. 1, 2005).
14. M. R. Aust, C. S. Madsen, A. Jennings, J. L. Kasperbauer, S. J. Gendler, Mucin mRNA expression in normal and vasomotor inferior turbinates. *Am J Rhinol* 11, 293 (July-August, 1997).
15. H. H. Jung, J. H. Lee, Y. T. Kim, S. D. Lee, J. H. Park, Expression of mucin genes in chronic ethmoiditis. *Am J Rhinol* 14, 163 (May-June, 2000).
16. M. Arumugam et al., Enterotypes of the human gut microbiome. *Nature* 473, 174 (May 12, 2011).
17. K. Honda, *Porphyromonas gingivalis* sinks teeth into the oral microbiota and periodontal disease. *Cell host & microbe* 10, 423 (Nov. 17, 2011).
18. A. Yuta, M. Ali, M. Sabol, E. Gaumond, J. N. Baraniuk, Mucoglycoprotein hypersecretion in allergic rhinitis and cystic fibrosis. *Am J Physiol* 273, L1203 (December, 1997).
19. P. J. Turnbaugh, F. Backhed, L. Fulton, J. I. Gordon, Diet-induced obesity is linked to marked but reversible alterations in the mouse distal gut microbiome. *Cell Host Microbe* 3, 213 (Apr. 17, 2008).
20. K. E. Fujimura et al., Man's best friend? The effect of pet ownership on house dust microbial communities. *J Allergy Clin Immunol* 126, 410 (August).
21. Y. J. Huang et al., A persistent and diverse airway microbiota present during chronic obstructive pulmonary disease exacerbations. *OMICS* 14, 9 (February).
22. M. J. Cox et al., *Lactobacillus casei* abundance is associated with profound shifts in the infant gut microbiome. *PLoS One* 5, e8745.
23. E. M. Bik et al., Bacterial diversity in the oral cavity of 10 healthy individuals. *ISME J* 4, 962 (August).
24. C. Palmer, E. M. Bik, D. B. DiGiulio, D. A. Relman, P. O. Brown, Development of the human infant intestinal microbiota. *PLoS Biol* 5, e177 (July, 2007).
25. P. J. Turnbaugh et al., Organismal, genetic, and transcriptional variation in the deeply sequenced gut microbiomes of identical twins. *Proc Natl Acad Sci USA* 107, 7503 (April 20).
26. Ivanov, I I et al., Induction of intestinal Th17 cells by segmented filamentous bacteria. *Cell* 139, 485 (Oct. 30, 2009).
27. K. Duan, C. Dammel, J. Stein, H. Rabin, M. G. Surette, Modulation of *Pseudomonas aeruginosa* gene expression by host microflora through interspecies communication. *Mol Microbiol* 50, 1477 (December, 2003).
28. J. Nishikawa, T. Kudo, S. Sakata, Y. Benno, T. Sugiyama, Diversity of mucosa-associated microbiota in active and inactive ulcerative colitis. *Scand J Gastroenterol* 44, 180 (2009).
29. S. I. Woo, J. Y. Kim, Y. J. Lee, N. S. Kim, Y. S. Hahn, Effect of *Lactobacillus sakei* supplementation in children with atopic eczema-dermatitis syndrome. *Ann Allergy Asthma Immunol* 104, 343 (April, 2010).
30. S. C. Corr et al., Bacteriocin production as a mechanism for the antiinfective activity of *Lactobacillus salivarius* UCC118. *Proc Natl Acad Sci USA* 104, 7617 (May 1, 2007).
31. A. Coffey et al., Use of a broad-host-range bacteriocin-producing *Lactococcus lactis* transconjugant as an alternative starter for salami manufacture. *Int J Food Microbiol* 43, 231 (Sep. 8, 1998).
32. S. Das et al., Cytokine amplification by respiratory syncytial virus infection in human nasal epithelial cells. *Laryngoscope* 115, 764 (May, 2005).
33. S. Sankaran-Walters et al., Epstein-Barr virus replication linked to B cell proliferation in inflamed areas of colonic mucosa of patients with inflammatory bowel disease. *J Clin Virol*, (October 27).
34. J. K. Hou, F. Velayos, N. Terrault, U. Mahadevan, Viral hepatitis and inflammatory bowel disease. *Inflamm Bowel Dis* 16, 925 (June).
35. R. C. Verdonk, E. B. Haagsma, J. H. Kleibeuker, G. Dijkstra, D. L. Sudan, Cytomegalovirus infection increases the risk for inflammatory bowel disease. *Am J Pathol* 176, 3098 (June).
36. K. Garborg, B. Waagsbo, A. Stallemo, J. Matre, A. Sundoy, Results of faecal donor instillation therapy for recurrent *Clostridium difficile*-associated diarrhoea. *Scand J Infect Dis* 42, 857 (December, 2010).
37. G. J. Leyer, S. Li, M. E. Mubasher, C. Reifer, A. C. Ouwehand, Probiotic effects on cold and influenza-like symptom incidence and duration in children. *Pediatrics* 124, e172 (August, 2009).
38. J. F. Piccirillo, M. G. Merritt, Jr., M. L. Richards, Psychometric and clinimetric validity of the 20-Item Sino-Nasal Outcome Test (SNOT-20). *Otolaryngol Head Neck Surg* 126, 41 (January, 2002).
39. F. C. Roediger et al., Nucleic acid extraction efficiency and bacterial recovery from maxillary sinus mucosal samples obtained by brushing or biopsy. *Am J Rhinol Allergy* 24, 263 (July-August).
40. E. L. Brodie et al., Application of a high-density oligonucleotide microarray approach to study bacterial population dynamics during uranium reduction and reoxidation. *Appl Environ Microbiol* 72, 6288 (September, 2006).
41. D. Lane, 16S/23S rRNA sequencing. G. M. Stackebrandt E, Ed., Nucleic acid techniques in bacterial systematics. (John Wiley & Sons., New York, 1991).
42. J. D. Storey, R. Tibshirani, Statistical significance for genomewide studies. *Proc Natl Acad Sci USA* 100, 9440 (Aug. 5, 2003).
43. M. N. Price, P. S. Dehal, A. P. Arkin, FastTree: computing large minimum evolution trees with profiles instead of a distance matrix. *Mol Biol Evol* 26, 1641 (July, 2009).
44. I. Letunic, P. Bork, Interactive Tree Of Life (iTOL): an online tool for phylogenetic tree display and annotation. *Bioinformatics* 23, 127 (Jan. 1, 2007).
45. K. Bomer et al., A mouse model of acute bacterial rhinosinusitis. *Arch Otolaryngol Head Neck Surg* 124, 1227 (November, 1998).
46. C. Blair, R. M. Naclerio, X. Yu, K. Thompson, A. Sperling, Role of type 1 T helper cells in the resolution of acute *Streptococcus pneumoniae* sinusitis: a mouse model. *J Infect Dis* 192, 1237 (Oct. 1, 2005).
47. M. H. Ahn et al., Titanium dioxide particle-induced goblet cell hyperplasia: association with mast cells and IL-13. *Respir Res* 6, 34 (2005).
48. G. Muyzer, E. C. de Waal, A. G. Uitterlinden, Profiling of complex microbial populations by denaturing gradient gel electrophoresis analysis of polymerase chain reaction-amplified genes coding for 16S rRNA. *Appl Environ Microbiol* 59, 695 (March, 1993).

What is claimed is:

1. A method of treating sinusitis in an individual in need thereof, the method comprising nasally administering to the individual a pharmaceutical composition comprising an effective amount of *Lactobacillus sakei* and an effective amount of *Streptococcus cristatus*; wherein the sinusitis comprises a *Corynebacterium* sinus infection; thereby treating the sinusitis in the individual.

2. The method of claim 1, wherein the *Corynebacterium* is *Corynebacterium tuberculostearicum*, *Corynebacterium segmentosum*, or a combination thereof.

3. The method of claim 1, wherein the *Lactobacillus sakei* colonizes the sinonasal mucosa of the individual.

4. The method of claim 3, wherein the sinonasal mucosa is the maxillary sinus.

5. The method of claim 1, wherein the pharmaceutical composition further comprises an effective amount of *Streptococcus constellatus, Streptococcus mutans, Streptococcus suis, Streptococcus thermophiles, Streptococcus downei, Lactococcus lactis*, or a combination of two or more thereof.

6. The method of claim 1, wherein the pharmaceutical composition is administered to a sinonasal mucosa in the individual.

7. The method of claim 1, wherein the sinusitis is chronic sinusitis.

8. The method of claim 1, wherein the pharmaceutical composition further comprises an effective amount of a bacterial species within a phylum and family selected from the group consisting of: Firmicutes Acholeplasmataceae; Firmicutes Acidaminococcus; Firmicutes Aerococcaceae; Firmicutes Bacillaceae; Firmicutes Carnobacteriaceae; Firmicutes Clostridiaceae; Firmicutes Enterococcaceae; Firmicutes Lachnospiraceae; Firmicutes Lactobacillaceae; Firmicutes Mycoplasmataceae; Firmicutes Mycoplasmataceae; Firmicutes Paenibacillaceae; Firmicutes Peptococcus; Firmicutes Staphylococcaceae; Firmicutes Streptococcaceae; Firmicutes Syntrophomonadaceae; Proteobacteria Bdellovibrionaceae; Proteobacteria Bradyrhizobiaceae; Proteobacteria Campylobacteraceae; Proteobacteria Desulfoarculaceae; Proteobacteria Desulfobacteraceae; Proteobacteria Helicobacteraceae; Proteobacteria Neisseriaceae; Proteobacteria Nitrospinaceae; Proteobacteria Pasteurellaceae; Proteobacteri a Polyangiaceae; Proteobacteria Sphingomonadaceae; Proteobacteria Syntrophobacteraceae; Bacteroidetes Flavobacteriacea; Bacteroidetes Flexibacteraceae; Bacteroidetes Porphyromonadaceae; Bacteroidetes Prevotelaceae; Bacteroidetes Rikenellaceae; Bacteroidetes Sphingobacteriaceae; Actinobacteria Micrococcaceae; Actinobacteria Acidimicrobiaceae; Planctomycetes Planctomycetaceae; Cynaobacteria Chloroplasts; Spirochaetes Spirochaetaceae; Chlorobi Chlorobiaceae; Fusobacteria Fusobacteriaceae; Verrucomicrobia Verrucomicrobiaceae; and a combination of two or more thereof.

9. A method of treating sinusitis in an individual in need thereof, the method comprising administering to the individual a pharmaceutical composition comprising an effective amount of *Lactobacillus sakei* and an effective amount of *Streptococcus cristatus*; wherein the sinusitis comprises *Corynebacterium tuberculostearicum*, thereby treating the sinusitis in the individual.

10. The method of claim 9, wherein the *Lactobacillus sakei* colonizes a sinonasal mucosa of the individual.

11. The method of claim 10, wherein the sinonasal mucosa is the maxillary sinus.

12. The method of claim 9, wherein the sinusitis further comprises *Corynebacterium segmentosum*.

13. The method of claim 9, comprising nasally administering the pharmaceutical composition to the individual.

14. The method of claim 9, wherein the pharmaceutical composition is administered trans-nasally or to the sinuses.

15. The method of claim 9, wherein the pharmaceutical composition is administered to the sinonasal mucosa in the individual.

16. The method of claim 9, wherein the pharmaceutical composition further comprises *Streptococcus constellatus, Streptococcus mutans, Streptococcus suis, Streptococcus thermophiles, Lactococcus lactis, Streptococcus downei*, or a combination of two or more thereof.

17. The method of claim 9, further comprising detecting the microbial diversity of the sinus mucosa of the individual.

18. The method of claim 9, further comprising detecting the relative level of *Corynebacterium tuberculostearicum* in a mucosal sample from the individual, and comparing the relative level of *Corynebacterium tuberculostearicum* in the sample to a control of *Corynebacterium tuberculostearicum* levels.

19. The method of claim 9, wherein the sinusitis is chronic sinusitis.

20. The method of claim 9, wherein the pharmaceutical composition further comprises an effective amount of a bacterial species within a phylum and family selected from the group consisting of: Firmicutes Acholeplasmataceae; Firmicutes Acidaminococcus; Firmicutes Aerococcaceae; Firmicutes Bacillaceae; Firmicutes Carnobacteriaceae; Firmicutes Clostridiaceae; Firmicutes Enterococcaceae; Firmicutes Lachnospiraceae; Firmicutes Lactobacillaceae; Firmicutes Mycoplasmataceae; Firmicutes Mycoplasmataceae; Firmicutes Paenibacillaceae; Firmicutes Peptococcus; Firmicutes Staphylococcaceae; Firmicutes Streptococcaceae; Firmicutes Syntrophomonadaceae; Proteobacteria Bdellovibrionaceae; Proteobacteria Bradyrhizobiaceae; Proteobacteria Campylobacteraceae; Proteobacteria Desulfoarculaceae; Proteobacteria Desulfobacteraceae; Proteobacteria Helicobacteraceae; Proteobacteria Neisseriaceae; Proteobacteria Nitrospinaceae; Proteobacteria Pasteurellaceae; Proteobacteri a Polyangiaceae; Proteobacteria Sphingomonadaceae; Proteobacteria Syntrophobacteraceae; Bacteroidetes Flavobacteriacea; Bacteroidetes Flexibacteraceae; Bacteroidetes Porphyromonadaceae; Bacteroidetes Prevotelaceae; Bacteroidetes Rikenellaceae; Bacteroidetes Sphingobacteriaceae; Actinobacteria Micrococcaceae; Actinobacteria Acidimicrobiaceae; Planctomycetes Planctomycetaceae; Cynaobacteria Chloroplasts; Spirochaetes Spirochaetaceae; Chlorobi Chlorobiaceae; Fusobacteria Fusobacteriaceae; Verrucomicrobia Verrucomicrobiaceae; and a combination of two or more thereof.

* * * * *